(12) United States Patent
Rapp et al.

(10) Patent No.: US 10,973,462 B2
(45) Date of Patent: Apr. 13, 2021

(54) FIBER OPTIC BASED DEVICES AND METHODS FOR MONITORING SOFT TISSUE

(71) Applicants: Scott J. Rapp, Mountain View, CA (US); Gary L. Rapp, Dublin, OH (US); Larry J. Rapp, Dublin, OH (US)

(72) Inventors: Scott J. Rapp, Mountain View, CA (US); Gary L. Rapp, Dublin, OH (US); Larry J. Rapp, Dublin, OH (US)

( * ) Notice: Subject to any disclaimer, the term of this patent is extended or adjusted under 35 U.S.C. 154(b) by 124 days.

(21) Appl. No.: 14/703,623

(22) Filed: May 4, 2015

(65) Prior Publication Data
US 2015/0313533 A1 Nov. 5, 2015

Related U.S. Application Data

(60) Provisional application No. 61/988,262, filed on May 4, 2014.

(51) Int. Cl.
| | | |
|---|---|---|
| *A61B 5/00* | (2006.01) | |
| *A61B 5/01* | (2006.01) | |
| *A61G 13/12* | (2006.01) | |

(52) U.S. Cl.
CPC .......... *A61B 5/6879* (2013.01); *A61B 5/0013* (2013.01); *A61B 5/0022* (2013.01); *A61B 5/0082* (2013.01); *A61B 5/01* (2013.01); *A61B 5/447* (2013.01); *A61B 5/4878* (2013.01); *A61B 5/6833* (2013.01); *A61B 5/6898* (2013.01); *A61B 5/743* (2013.01); *A61B 2562/0247* (2013.01); *A61B 2562/0266* (2013.01); *A61B 2562/046* (2013.01); *A61B 2576/00* (2013.01); *A61G 13/12* (2013.01)

(58) Field of Classification Search
CPC ... A61B 5/0084; A61B 5/0059; A61B 5/6879; A61B 5/4878; A61B 5/01; A61B 5/0082; A61B 5/47; A61B 5/6833; A61B 5/6898; A61B 5/743; A61B 5/0013; A61B 5/0022; A61B 2562/0247; A61B 2562/0266; A61B 2562/046; A61B 2576/00; A61G 13/12
See application file for complete search history.

(56) References Cited

U.S. PATENT DOCUMENTS

| | | | |
|---|---|---|---|
| 2003/0216663 A1* | 11/2003 | Jersey-Willuhn | A61B 5/0536 600/547 |
| 2008/0255629 A1* | 10/2008 | Jenson | A61B 5/6857 607/19 |
| 2012/0070112 A1* | 3/2012 | Mitachi | A61B 5/113 385/13 |
| 2012/0071731 A1* | 3/2012 | Gottesman | A61B 5/6833 600/301 |
| 2012/0190989 A1* | 7/2012 | Kaiser | A61B 5/0031 600/476 |
| 2013/0300431 A1* | 11/2013 | Beinhocker | G02B 6/4469 324/539 |
| 2015/0141854 A1* | 5/2015 | Eberle | A61B 5/02154 600/488 |
| 2016/0107309 A1* | 4/2016 | Walsh | B25J 9/0006 248/550 |

* cited by examiner

*Primary Examiner* — Hien N Nguyen
(74) *Attorney, Agent, or Firm* — Business Patent Law, PLLC; Kenneth F. Pearce

(57) ABSTRACT

Fiber optic based systems and related components and methods for monitoring soft tissue volume (pressure) and temperature change.

20 Claims, 24 Drawing Sheets

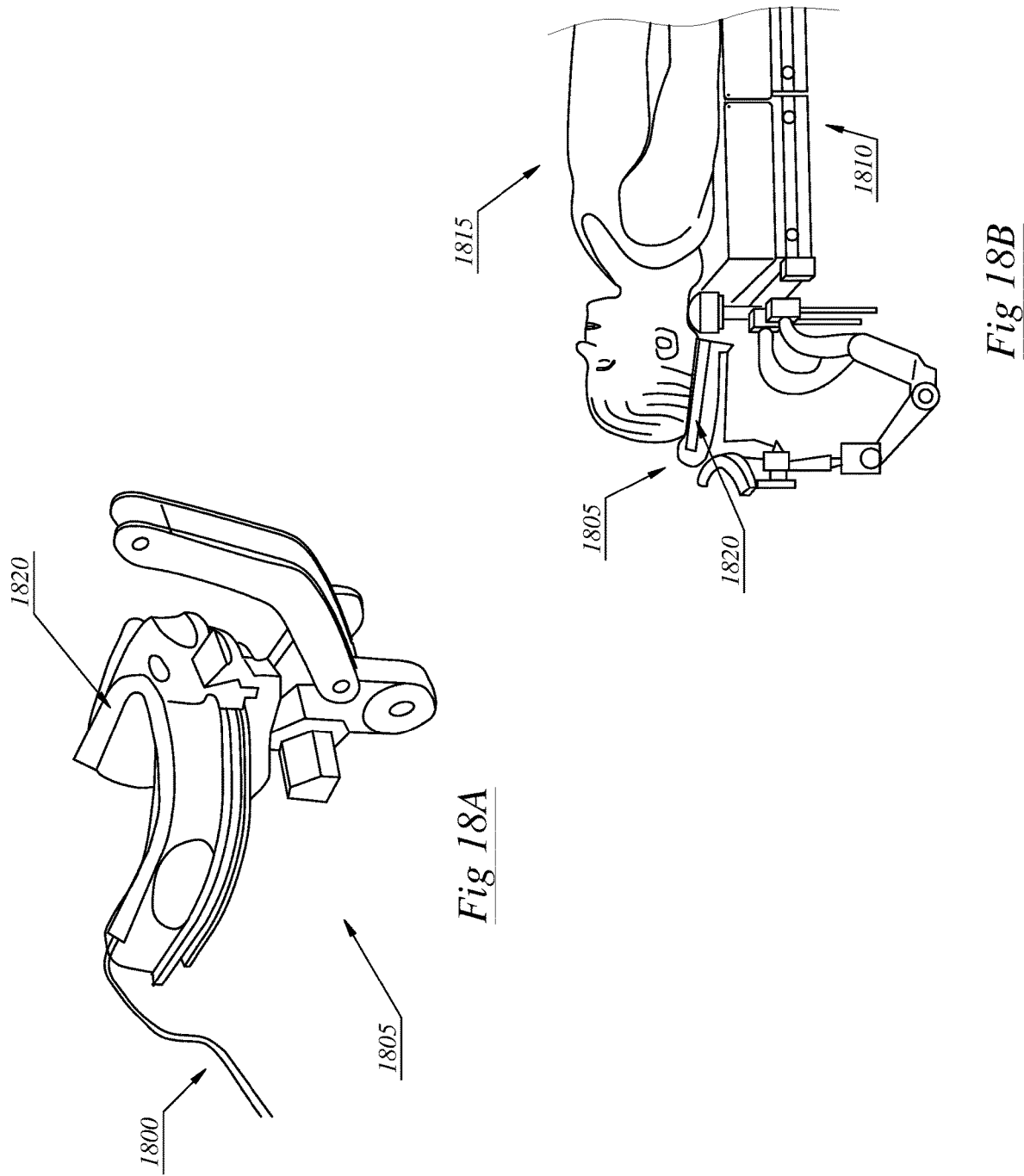

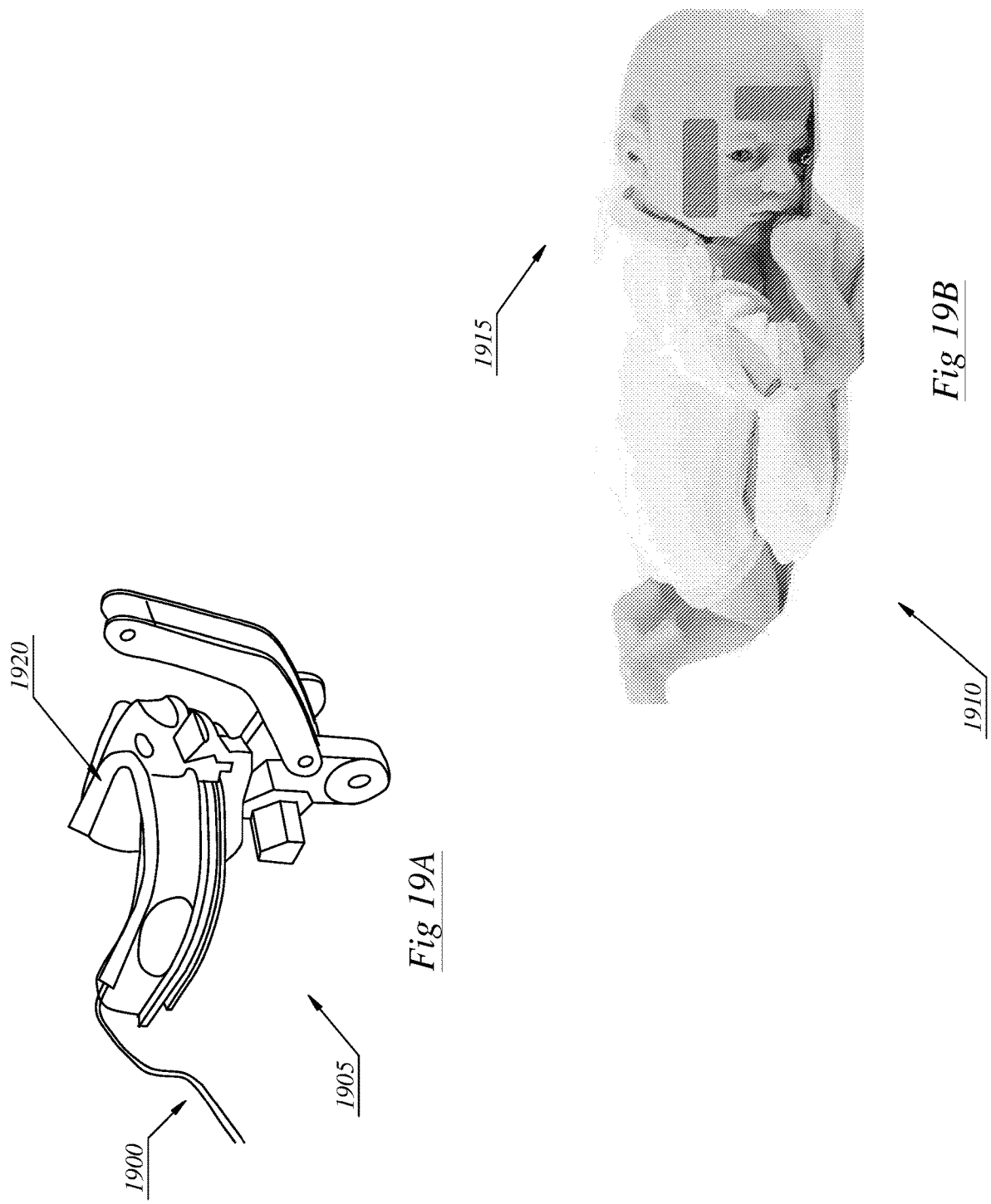

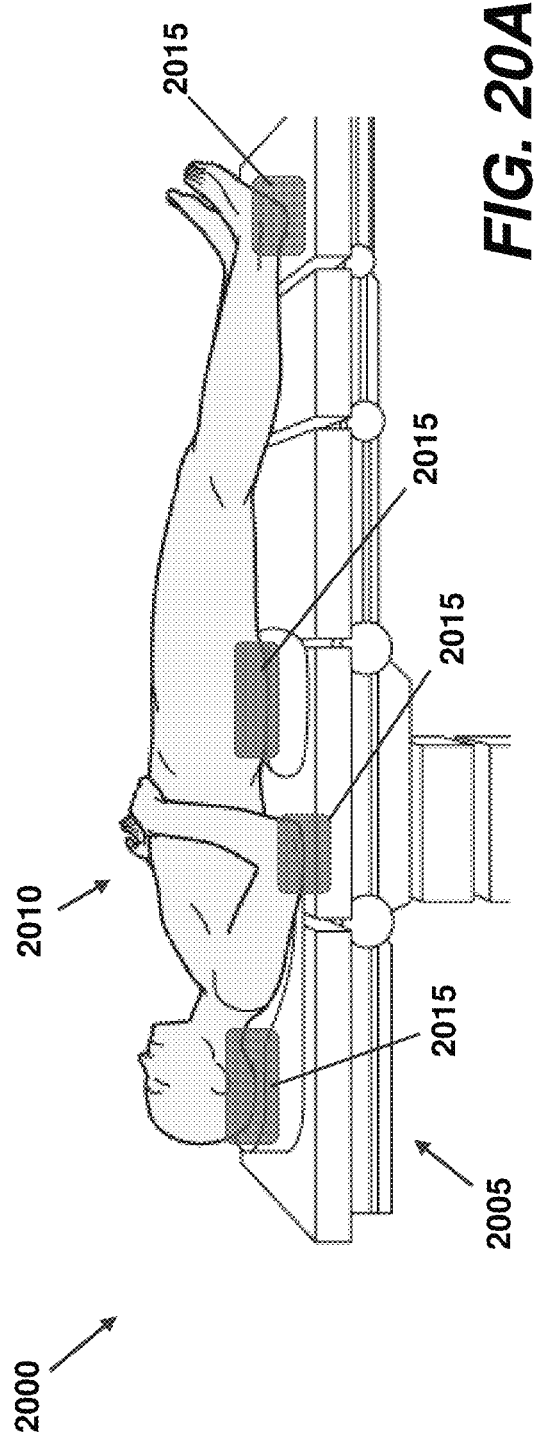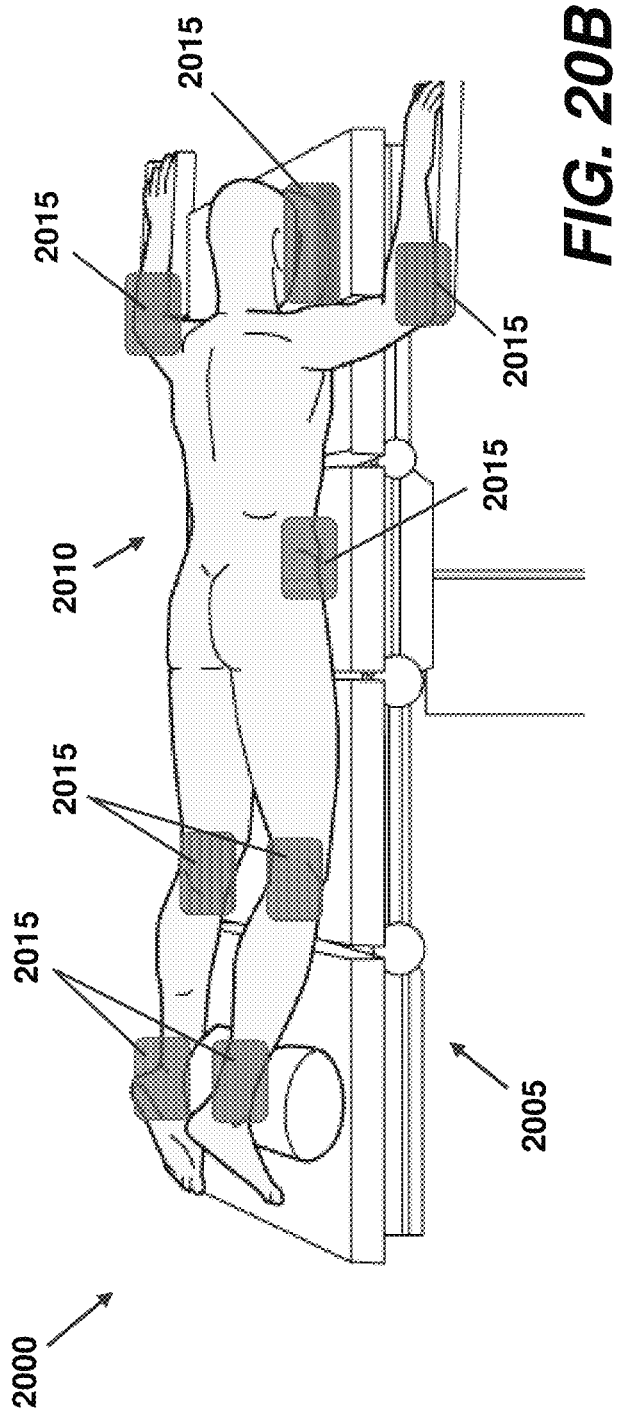

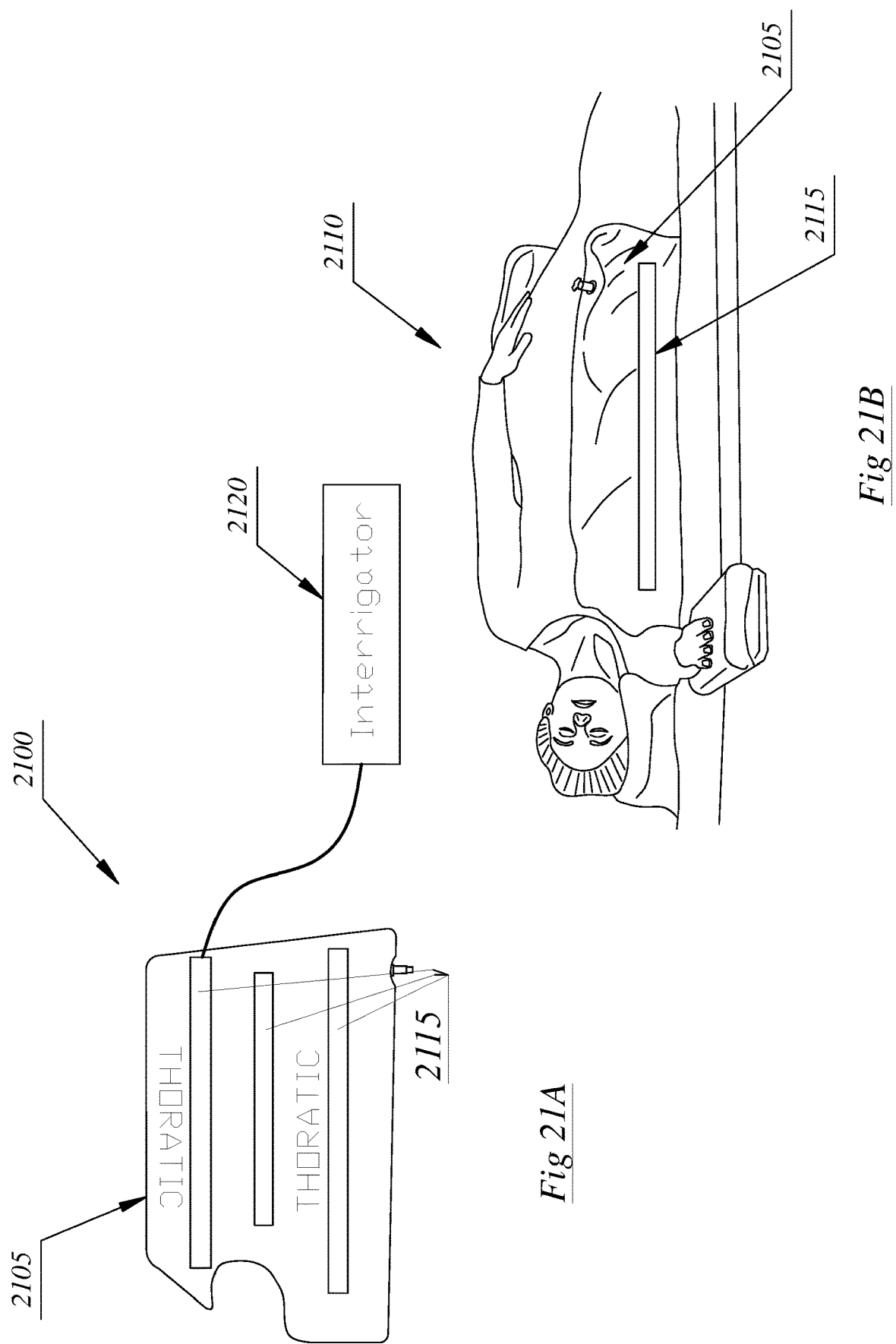

FIBER OPTIC BASED DEVICES AND METHODS FOR MONITORING SOFT TISSUE

CROSS-REFERENCE TO RELATED APPLICATIONS

This application claims the benefit to U.S. Provisional Application No. 61/988,262, filed on May 4, 2014, which is hereby incorporated by reference as if fully recited herein.

TECHNICAL FIELD

The general inventive concepts discussed in this disclosure relate, among other things, to optical sensors and, more particularly, to devices and methods for using light to monitor soft tissue.

BACKGROUND

Soft tissue edema results from increased capillary permeability and subsequent leakage of intravascular contents into the interstitium with a rise in intra and extra compartmental tissue pressures. The increase fluid extravasation clinically manifests with dolor (pain), calor (heat), hyperemia, decreased range of motion, and swelling. Excessive fluid within the interstitial tissues can lead to "pitting" or "non-pitting" edema, terms describing the lasting imprint of a particular compressive force applied to the region.

The most common etiology to clinical edema results from the activation of the inflammatory cascade. Inflammation leads to changes to within the vascular structures leading to dilation and increased permeability resulting from cellular and plasma mediated components. Cellular invasion and degranulation of leukocytes and macrophages leads to release of cytokine and chemokine factors further leading to local tissue disruption and permeability. Plasma mediated contributors activate the bradykinin system responsible for pain and complement system further leading to vessel dilation and cellular death.

The Starling's equation can be used to predict how the homeostasis of fluid will shift during inflammation leading to edema: $J_v = K_{fc}[(P_c - P_t) - \sigma(\pi_p - \pi_t)]$ where $K_{fc}$ is the filtration coefficient of the capillary wall, $P_c$ is the capillary pressure, $P_t$ is the tissue pressure, a is a constant for a given tissue, $\pi_t$ is the colloid oncotic tissue pressure, and $\pi_p$ is the colloid oncotic plasma pressure.

Trauma represents the most common source of inflammation from soft tissue injury with injuries leading to over 6 million deaths in the United States alone and a conservative cost to health care of 27 billion dollars annually. Other sources of inflammation can occur from infection, thermal or chemical or burn injury, frostbite, allergic response to stimulus, and foreign body. Chronic forms of edema and swelling can arise from conditions such as lymphatic disorders, congestive heart failure, end-stage renal disease, venous hypertension, connective tissue disorders and myxedema, and hypertension.

Traumatic fractures to bones are associated with extensive soft tissue swelling and edema. Long bone fractures in the pediatric population are common. Secondary complications from edema and swelling following bone reduction and immobilization are frequent with as high as 28% incidence of skin following casting. Moreover, the overall hospital-associated cost to the patient to have the cast reapplied was in excess of $10,000.

Applying the correct amount of tension of casting materials during this time is largely anecdotally based on experience of the applier with a small margin of error to ensure success. Apply a cast too loose, and the young patient often ends up back in the emergency room that evening with the parents holding the cast. Applying too tight can result in less room for further inflammation and swelling thus leading to tissue ischemia, skin breakdown, and ulceration.

Supracondylar fractures represent a common subset of humeral fractures and currently represent the most common above the elbow fracture in the pediatric population. They represent 3-18% of all fractures, 60% above the elbow fractures, and two-thirds of children hospitalized for elbow injuries are due to this. The prevalence of displaced supracondylar humeral fractures presenting with vascular compromise has been reported to be up to 20%.

The treatment approach to this injury garners much discussion and debate today largely due to historically high rates of nonunion, malunion, incidence of compartment syndrome leading to Volkmann's contracture, and overall technical difficulties regarding success of the reduction through closed and open approaches.

Edema in itself is a normal process for defending against pathogens to lead to tissue healing and regeneration. However, when the insult is severe enough, the effects of soft tissue edema can lead to hypo-perfusion, ischemia, and ultimately tissue death. The most common or feared is microcirculatory compromise or compartment syndrome.

First described in the early $19_{th}$ century, acute compartment syndrome results from increased pressures in an anatomically definable closed-fascial space. The pathophysiology arises when the tissue pressure, usually 0 to 8 mmHg, is increased above capillary perfusion pressures of 30 mmHg or more for extended periods of time. Usually a result of extremity trauma, crush injury, prolonged tissue compression, or reperfusion injury, compartment syndrome can lead to muscle ischemia in as little as six hours. If left untreated, further increases in pressure from arterial inflow and diminished outflow can lead to muscle necrosis, fibrosis, and muscle death. To compound the problem, treating compartment syndrome after a delay in intervention can lead to reperfusion injury as ischemic tissue sustains an inflammatory response with further exacerbation of swelling or edema.

Traditional symptoms of compartment syndrome are pain out of proportion to exam, pain with passive stretch, skin pallor, and diminished or loss of pulses, with paraesthesias and poikilothermia being late findings. Clinical exam findings are often unreliable, however, and in the pediatric, non-verbal, obtunded, or anesthetic population, diagnosis can be quite challenging. With very few objective measurements that can be utilized for monitoring, diagnosis, or prevention, compartment syndrome can lead to irreparable tissue damage if left untreated. If diagnosed in the early phase, the current surgical intervention involves the release of compartmental pressures through the opening of the restrictive tissue with fasciotomies. Once swelling or insult has subsided, the resultant defect may be closed in a delayed fashion or a skin graft may be warranted, both of which typically result in prolonged hospital courses, wound care, and medical costs.

Even more catastrophic sequela is the development of a Volkmann's contracture when compartment syndrome is left unrecognized and untreated. Scarred muscle from ischemic injury is replaced by fibrotic, non-functioning tissue. Greater than 60% of patients require on average four or more reconstructive operations involving muscle/tendon transfers, tendon lengthening procedures, tendon slides, and free tissue transfer. All reconstructive options lead to poor outcomes.

Many studies have looked at the frequency of compartment syndrome in traumatic fractures. One recent study looked at reported compartment syndrome in both open and closed fractures after sampling the National Pediatric Trauma Registry from October 1995 to January 2000. Within this time frame at 90 pediatric trauma centers, there were 133 reported cases of extremity compartment syndrome in hospitalized trauma patients. The majority of these fractures were closed on initial presentation with 95.4% requiring surgical intervention.

A diagnosis of compartment syndrome also carries a high risk of malpractice claims regardless of timing and intervention after diagnosis. One study evaluated the orthopedic claims of one large insurance company in one state from 1980 to 2003. 19 claims involving 16 cases led to a 56% indemnity payment. The average indemnity payment was $426,000, much higher than the overall orthopedic indemnity payment of $136,000. The majority of plaintiffs argued that the symptoms "failed to impress" in that the physician did not pursue further action with subtle findings such as numbness or reduced range of motion. A delay in the time to fasciotomy was significantly associated with an increased amount of indemnity payment.

A second study in the United Kingdom evaluated claims in the adult population and found that in over a 6-year period, there were 33 claims involving compartment syndrome and the question of its management. The average payment for delayed diagnosis of compartment syndrome was $355,863, with total payments of $11,743,839.

Technologies that attempt to capture pressure from increased edema and swelling are on the market today. Intracorpreal catheter placement is one such technology. In intracorpreal catheter placement, a large bore needle is inserted into the compartment of interest and a small amount of fluid is injected to allow a transduced reading. Effective at capturing the pressure to the deep compartment, the device is user dependent. For example, a false reading can occur if the needle is not placed in the right location. As another example, an erroneous (e.g., elevated) reading can occur if too much fluid is injected or pressed up against more dense tissue (bone/fascia over muscle). Moreover, the device causes measurable pain to the patient (already usually quite uncomfortable) since the tissue needs to be punctured by a large needle. The need to keep the patient (e.g., a child) from moving his arm or leg with muscle contraction is another limiting factor.

Electrical cast monitoring is another technology being pursued. A similar technology, which was initially developed to monitor breathing patterns, involves capacitive and piezoresistive textiles manufactured to act as a conforming fabric. This technology has also been reported to be applicable to cast lining to help determine strain and force.

A major concern of these types of technologies relates to the use of an electrical current to assist in pressure determination. In the pediatric population, keeping a cast or splint devoid of any moisture while placed on a patient can be very challenging and the safety and/or durability of the above technologies in common everyday use with children is unclear. Conversely, the inventive fiberoptic pressure monitoring system uses wavelengths of light to determine pressure and the fibers can be safely exposed to harsh environments.

Yet another technology in use is the near infra-red spectroscopy (NIRS) measuring tissue oxygenation (STo2). This technology shows promise in sensing tissue-specific perfusion; however, the results are not necessarily standardized. Limiting drawbacks also include overall cost, as well as measurements that may be influenced by skin pigmentation, direct light exposure, myoglobin presence, reduced ability to bend the sensors, and need for direct skin contact at all times.

The use of optical sensors for measuring force and temperature is known. For example, WO 2013/071351 discloses such an optical sensing apparatus, which may be used to measure pressures in the human body. In the '351 application, the sensing apparatus uses a pair of optical fibers which are wound around one another to form a double helical structure. Each optical fiber has a series of Bragg gratings (FBGs). The apparatus includes a series of sensing regions at which the FBGs are located. In particular, the fibers and the FBGs are oriented in a direction of the applied force to maximize the response of the sensing regions. A change in force at the sensing regions results in a change in strain in the FBGs of the sensing regions. The change in strain can be ascertained by detecting an optical response using an optical analyzer. Nonetheless, there remains an unmet need for an improved optical sensing apparatus for monitoring soft tissue.

SUMMARY

Given the various shortcomings of the existing technologies, there exists a need for a technology that can help to prevent the consequences of severe edema, thereby facilitating improvised and objectively supported medical decision making, prevention of secondary detrimental outcomes, and reduction in overall healthcare costs to patients, hospital systems, and insurance companies. This will be accomplished, at least in part, by reducing error resulting from personal "judgment" and "gestalt" on the part of a health care provider when dealing with rapidly expanding swelling and subsequent adverse outcomes related to long periods of increased tissue pressure in an extremity.

Thus, to provide a more cost-effective, accurate/sensitive, safe, durable, and/or flexible means for monitoring pressure and/or temperature changes in soft tissue, general inventive concepts of the disclosure are directed to devices, systems, and methods for monitoring soft tissue volume and temperature change such as seen with tissue edema resulting from acute trauma, interstitial hypertension, iatrogenic post-infusion injury, and post-surgical sequelae. The rate of evolving edema is measured through fiber optic sensors placed on the skin surface of a patient to ultimately reduce secondary complications of dolor, skin breakdown, compartment syndrome, and tissue ischemia or death. As a result, the general inventive concepts allow for several applications to improve the decision-making capacity of a clinician toward the appropriate intervention.

While the general inventive concepts (e.g., fiber optic sensors) will find particular applicability in the trauma and peri-operative setting, the inventive technology could also be used in other applications. For example, lining pressure garments and orthotics of burn patients may allow for optimal pressure application when treating or preventing hypertrophic scars after large skin grafts. Additionally, such fiber optic sensors could also be used to line extremity compression garments used in peripheral edema to provide detailed assessment of relevant tissue pressure.

By way of example and to illustrate various aspects of the general inventive concepts, devices and/or methods for monitoring soft tissue volume and temperature change are disclosed herein.

Exemplary fiber optic sensors contemplated by the general inventive concepts represent technical improvements over conventional optical sensors. For example, the fiber itself (versus point sensors such as those resulting from the use of FBGs) forms the sensor. Additionally, a single fiber can be utilized. Thus, a true distributed sensing apparatus that provides better spatial resolution, lower manufacturing and/or implementation costs, and/or a simpler, more flexible design is disclosed.

In certain exemplary embodiments, a device for monitoring a pressure and/or a temperature of soft tissue is provided.

In certain exemplary embodiments, a system for monitoring a pressure and/or a temperature of soft tissue is provided.

In certain exemplary embodiments, a method of monitoring a pressure and/or a temperature of soft tissue is provided.

Other aspects and features of the invention will become apparent to those skilled in the art upon review of the following detailed description of exemplary embodiments along with the accompanying drawing figures.

BRIEF DESCRIPTION OF THE DRAWINGS

In the following descriptions of the drawings and exemplary embodiments, like reference numerals across the several views refer to identical or equivalent features, and:

FIGS. 18A and 18B illustrate one exemplary embodiment of a soft tissue monitoring system for use in an operating room, particularly in conjunction with the headrest of an operating table;

FIGS. 19A and 19B illustrate another exemplary embodiment of a soft tissue monitoring system for use in an operating room, particularly in conjunction with the headrest of an operating table that is used to support the head of a patient from the front;

FIGS. 20A and 20B illustrate another exemplary embodiment of a soft tissue monitoring system for use in an operating room, particularly in conjunction with an operating table for monitoring various pressure points on the patient's body in a supine or prone position;

FIGS. 21A and 21B illustrate another exemplary embodiment of a soft tissue monitoring system for use in an operating room, particularly in conjunction with a surgical beanbag;

DETAILED DESCRIPTION OF THE EXEMPLARY EMBODIMENTS

Figure 1:
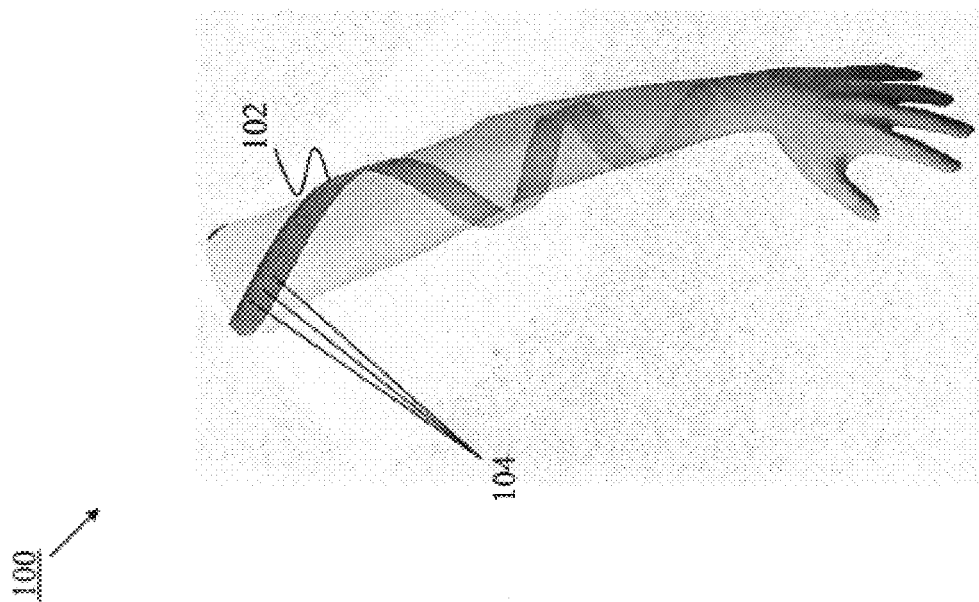
FIG. 1 illustrates an optical sensor in the form of a flexible tape, according to one exemplary embodiment.

While the general inventive concepts are susceptible of embodiment in many different forms, there are shown in the drawings, and will be described herein in detail, exemplary embodiments thereof with the understanding that the present disclosure is to be considered as merely an exemplification of the principles of the general inventive concepts. Accordingly, the general inventive concepts are not intended to be limited to the particular exemplary embodiments illustrated herein.

As shown in FIG. 1, one exemplary embodiment of a device 100 for monitoring soft tissue temperature and/or pressure includes one or more optical sensors (e.g., fiber optic strands, cables, or the like) that are embedded in or otherwise interfaced with a tape 102, ribbon, or the like to be placed on an extremity or body region. The tape 102 can be spirally wrapped around an arm, forearm, leg, thigh, abdomen, or head of a subject. In one exemplary embodiment, the tape 102 is able to maintain contact with the underlying skin due to an adhesive placed on the side in contact with skin.

In one exemplary embodiment, multiple parallel fiber optic strands 104 are embedded within the tape 102. The fiber optic strands 104 are placed at an equal distance from each other running the entire length of the tape 102.

In one exemplary embodiment, the fiber optic strands 104 converge together at a point that is housed in a plastic adapter (not shown). The adapter allows the device 100 to interface with other related equipment, such as described herein.

In one exemplary embodiment, the tape 102 is moisture resistant, if not waterproof.

The configuration array of the optical sensors (e.g., the fiber optic strands 104) may be fashioned in other suitable arrangements, such as a matrix, spiral, honeycomb, double layer, or any other configuration that provides the desired coverage for the tissue to be monitored.

Figure 2:
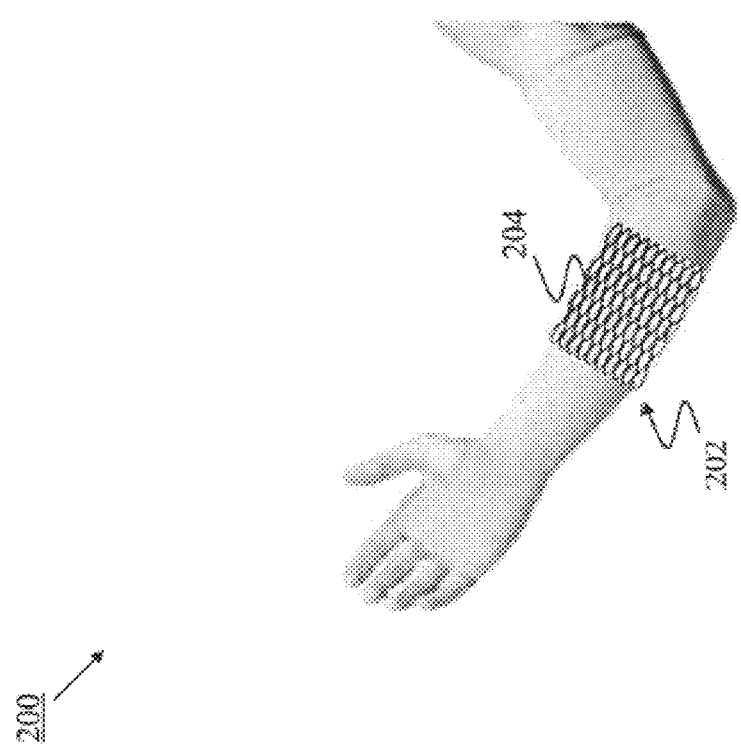
FIG. 2 illustrates an optical sensor in the form of a flexible fabric, according to one exemplary embodiment.

In one exemplary embodiment, a device 200 for monitoring soft tissue temperature and/or pressure includes one or more optical sensors (e.g., fiber optic strands, cables, or the like) that are embedded in or otherwise interfaced with a fabric 202 or the like to be placed on an extremity or body region. As shown in FIG. 2, the fabric 202 can form a honey-comb matrix 204 to be placed around a forearm within a fabric sleeve (not shown). The fabric 202 can be vertically oriented to allow for bi-laminar fiber layers that allow for readings with no fixed point of reference (such as in a cast). The fabric sleeve ensures that the honey-comb matrix 204 maintains contact with the underlying skin.

In one exemplary embodiment, the fiber optic strands 104 converge together at a point that is housed in a plastic adapter (not shown). The adapter allows the device 200 to interface with other related equipment, such as described herein.

In one exemplary embodiment, the fabric 202 is moisture resistant, if not waterproof.

Figure 3:
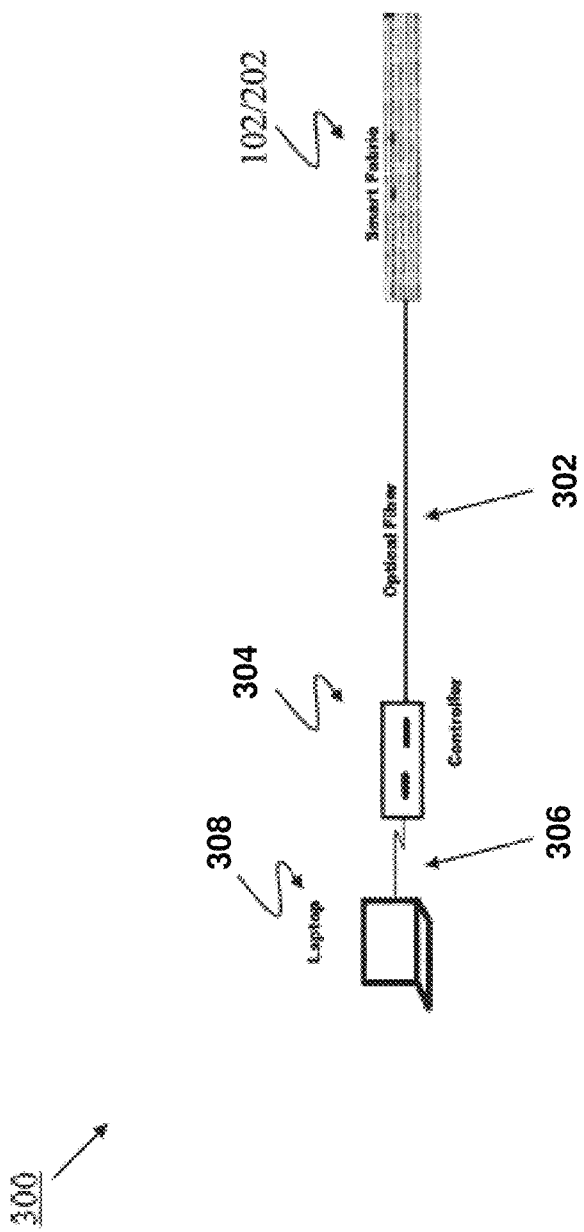
FIG. 3 is a diagram depicting one exemplary embodiment of a soft tissue measuring system.

In one exemplary embodiment, a system 300 for monitoring soft tissue temperature and/or pressure utilizes an optical sensor, such as the tape 102 or fabric 202 described herein. As shown in FIG. 3, the system 300 includes the fabric 202 as an exemplary optical sensor, an optical fiber 302, a controller 304, an interface 306, and a data processing device 308.

The optical fiber 302 connects the controller 304 and the fabric 202, such that light delivered to the fabric 202 can be returned or otherwise collected from the fabric 202 by the controller 304 for further processing. The collection of information from the fabric 202 by the controller 304 can be continuous, periodic, or event-driven (e.g., based on predefined thresholds).

In one exemplary embodiment, the fiber optic strands 104 converged within the adapter are connected to a light energy source. Non-limiting examples of light energy sources that may be suitable include lasers, ultraviolet light generators, or light-emitting diodes. In one exemplary embodiment, the light source (e.g., laser) is integrated with the controller 304, such that the controller 304 delivers light to the fabric 202 using the optical fiber 302.

Light is pulsed sequentially into the strands and reflections/transmissions are monitored by the controller 304 as a function of time, wavelength, and intensity. The time value defines the measurement location and the wavelength and intensity values determine temperature and pressure respectively. The amount of light reflected back will be captured by the controller 304 and recorded as a baseline measurement. As noted above, the measurements can be taken continuously or intermittently through the direct connection by the optical fiber 302.

Figure 4:
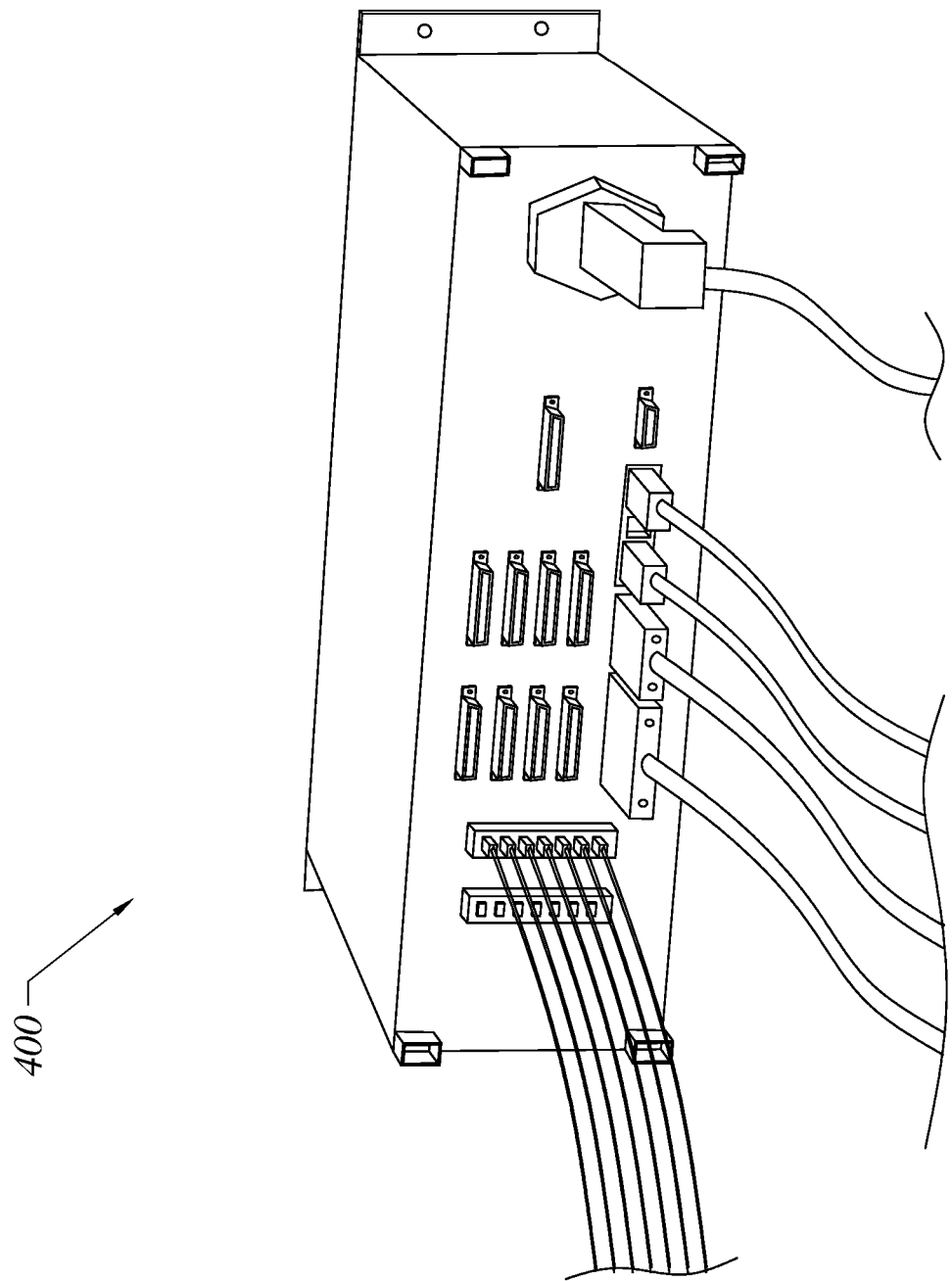
FIG. 4 illustrates one exemplary embodiment of a portable soft tissue measuring system (inside a case)

The data processing device 308 is connected to the controller 304 by the interface 306. In one exemplary embodiment, the interface 306 is a wired network or communication connection. In one exemplary embodiment, the interface 306 is a wireless network or communication connection. In one exemplary embodiment, the data processing device 308 is a general purpose computer. In one exemplary embodiment, the data processing device 308 is a portable processing device, such as a laptop or tablet. In this case, the entire system 300 could be designed to be portable such that it could be readily stored in a case 400 (see FIG. 4) for storage and/or transportation. In one exemplary embodiment, the data processing device 308 and the controller 304 are integrated, which could further promote the portability of the system 300.

The data processing device 308 includes software capable of processing the time, wavelength, and intensity information collected by the controller 304. The data processing device 308 will typically include a display (e.g., a monitor or the like) for outputting the collected information as well as information (e.g., reports, graphs) based thereon. The data processing device 308 could also include an audio means, such as a speaker, for outputting an alarm or other audible indicator if a measured change (e.g., a pressure) in the tissue exceeds a predefined threshold.

Figure 5:
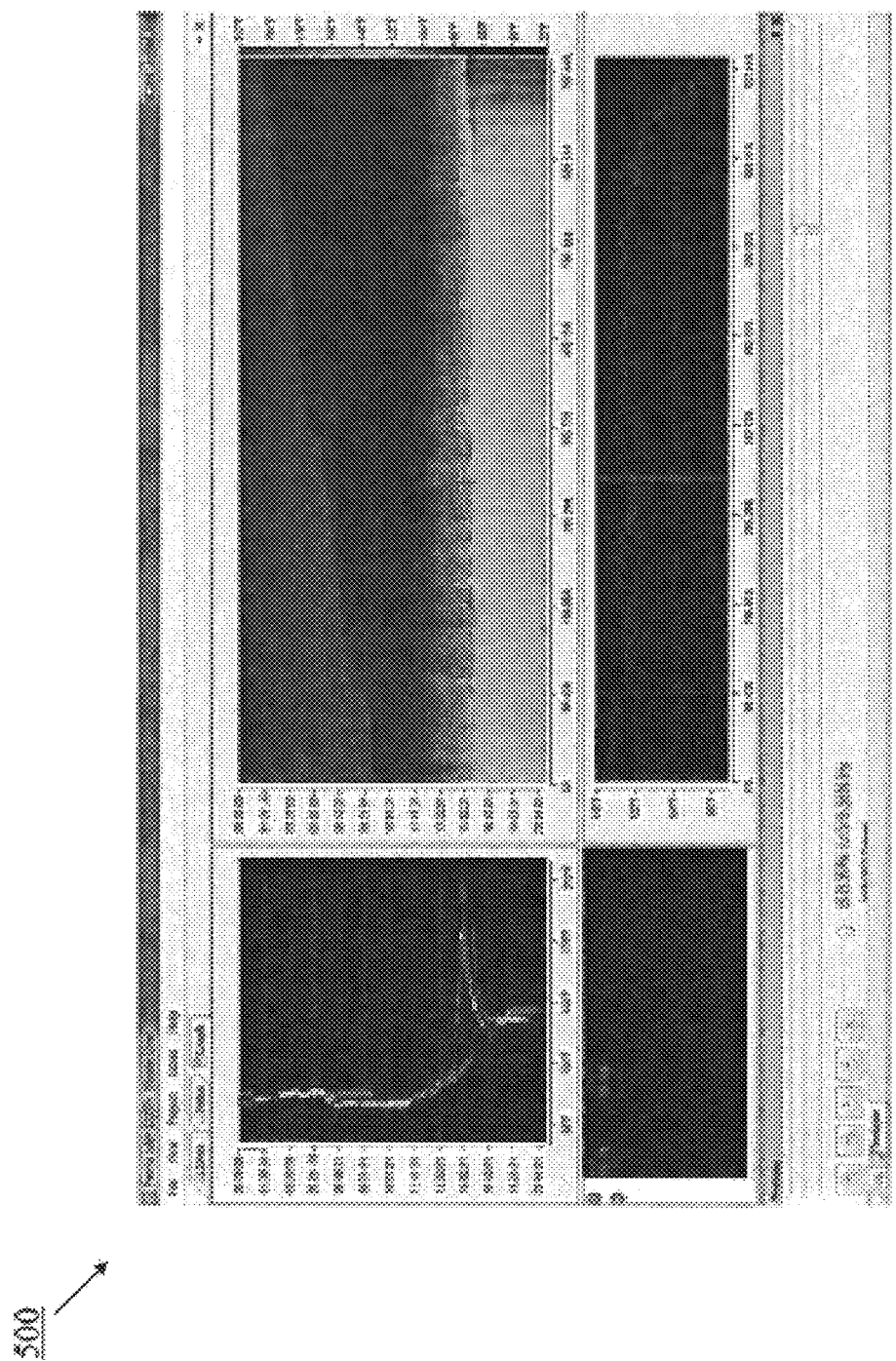
FIG. 5 represents an exemplary user interface displaying temperature and pressure readings at exact points over the length of one exemplary individual fiber optic strand.

In one exemplary embodiment, the data processing device 308 includes a user interface to facilitate interaction with an operator (e.g., doctor, nurse, technician). For example, the user interface could display a 3-D map indicating where there is light reflection and determine strain and pressure readings precisely with spatial recognition along the fiber optic strands. As shown in FIG. 5, the user interface could display a graph 500, report, or the like indicating temperature and pressure readings at exact points over the length of an individual fiber optic strand. The user interface may also have communications (e.g., cellular, Internet) capability to send data to a monitoring center located elsewhere.

In accordance with one exemplary methodology, as the volume and diameter of the tissue changes from edema or swelling, strain will be placed on the optical sensor, such as one having a spiral configuration (see FIG. 1), thereby changing (e.g., elongating or shortening) the spiral length. A repeat measurement of the amount of light returned can be measured. The rate of change between measurements may then be determined. If the rate of change is above a standardized limit for acceptable rates of change, an alarm will be set off. Temperature to the underlying tissue may also be recorded through a function of rate of light return. If the tissue in question has a large change in baseline temperature readings, an alarm can sound.

The following description of the underlying technical principles are intended to further illustrate the general inventive concepts and the specific exemplary embodiments disclosed herein.

Temperature and pressure sensors are generally defined as electronic devices (e.g., thermistors, thermal elements, pressure gauges, etc.) that measure a selective temperature or pressure value at a specific location. However, this approach is not practical if measuring the temperature or pressure of an area where hundreds of locations need to be monitored.

Quartz glass is a form of silicon dioxide ($SiO_2$) with amorphous solid structure. Pressure effects induce lattice oscillations within the solid. When light falls onto these pressure excited molecular oscillations, an interaction occurs between the light particles (photons) and the electrons of the molecule. A molecular vibration with the glass fiber material leads to light scattering (e.g., Rayleigh, Raman, or Brillouin scattering) of the laser light. The light is reflected back to its source and the shift in the wavelengths (Stokes, anti-Stokes line) is compared to a reference value. The intensity of the anti-Stokes band is pressure dependent, while the Stokes band is practically independent of pressure. The local pressure of the optical fiber is derived from the ratio of the anti-Stokes and Stokes light intensities. This intensity value of light is proportional to the molecular vibration created by pressure, allowing for the pressure at linear locations of the glass fiber cable to be calculated.

Spatial Resolution or location is determined by the amount of time it takes for the backscattered light to return to the detection unit in the DPS.

In particular, the general inventive concepts may encompass a compact, lightweight high-performance DPS system. The system is capable of delivering the required pressure and spatial resolution and high Signal-to-Noise ratio (SNR), while using commercial off-the-shelf (COTS) telecom grade components.

When an electromagnetic wave is launched into an optical fiber, the light is redistributed by various mechanisms in the form of Rayleigh, Raman, or Brillouin scattering. If the local pressure and temperature vibration and acoustic wave changes are relayed to the optical fibers, the scattered signal in the fiber is modulated by these physical parameters, and by measuring the changes of modulated signal, one can realize or form distributed fiber sensors. If the input light is a pulsed signal with a measurable pulse width, then the location of the modulated signal along the optical fiber can be measured by the time delay of the speed of light. The location accuracy is called spatial resolution. Depending on various characteristics of the 3 scattering techniques, a sensor with spatial resolution of a centimeter and high precision of measurement can be obtained.

There are two basic principles of measurement for distributed sensing technology, OTDR (Optical Time Domain Reflectometry) and OFDR (Optical Frequency Domain Reflectometry). For Distributed Temperature Sensing often a Code Correlation technology is employed which carries elements from both principles. See, for example, Bao and Chen, *Recent Progress in Distributed Fiber Optic Sensors*, Sensors 12:8601-8639 (2012), the entire disclosure of which forms part of the instant patent application and is presented in attached Appendix A.

OTDR was developed more than 20 years ago and has become the industry standard for telecom loss measurements which detects the (compared to Raman signal very dominant) Rayleigh backscattering signals. The principle for OTDR is quite simple and is very similar to the time of flight measurement used for radar. Essentially a narrow laser pulse generated either by semiconductor or solid state lasers is sent into the fiber and the backscattered light is analyzed. From the time it takes the backscattered light to return to the detection unit it is possible to locate the location of the temperature event.

Alternative DPS evaluation units deploy the method of Optical Frequency Domain Reflectometry (OFDR). The OFDR system provides information on the local characteristic only when the backscatter signal detected during the entire measurement time is measured as a function of frequency in a complex fashion, and then subjected to Fourier transformation. The essential principles of OFDR technology are the quasi continuous wave mode employed by the laser and the narrow-band detection of the optical back scatter signal. This is offset by the technically difficult measurement of the Raman scatter light and rather complex signal processing, due to the FFT calculation with higher linearity requirements for the electronic components.

Code Correlation DPS sends on/off sequences of limited length into the fiber. In contrast to OTDR technology, the optical energy is spread over a code rather than packed into a single pulse. Thus a light source with lower peak power compared to OTDR technology can be used, e.g., long life compact semiconductor lasers. The detected backscatter needs to be transformed (similar to OFDR technology) back into a spatial profile, e.g., by cross-correlation. In contrast to OFDR technology, the emission is finite (e.g., 128 bit) which avoids that weak scattered signals from far are superposed by strong scattered signals from short distance, improving the shot noise and the signal-to-noise ratio.

Using these techniques it is possible to analyze distances of greater than 30 km from one system and to measure temperature resolutions of less than 0.01° C.

In general, a distributed sensor can replace many point sensors. As a result it is the most cost effective, and weight and space efficient, sensor system available, as it only requires one fiber capable for sending and receiving the signal from the same fiber, and only one monitor is adequate to display the local changes in pressure or temperature. This considerable light weight advantage makes distributed sensors based on light scattering in optical fiber the most powerful monitoring option even in comparison to point fiber sensors, especially for medical field monitoring. Each method and principle of measurement has its applications and limitations. For example, advances in photon counting have allowed Raman systems to improve their spatial resolution to less than 1 cm.

The general inventive concepts includes methods for measuring pressure (and optionally temperature), such as in medical applications, wherein the sensory technology used in the methods is formulated based on precision, spatial resolution, cost, minimal sensing range, minimal measurement time, pressure accuracy, as well as other considerations. In depth descriptions of the Raman, Rayleigh, and Brillouin scattering methods, along with limitations and strengths of each are presented in the aforementioned publication. See *Recent Progress in Distributed Fiber Optic Sensors*, supra.

In view of the above, fiber-based sensors enjoy a significant edge over their electronic counterparts in cost as well as in the critical parameters of Size, Weight, and Power (SWAP). They are well suited for use near sensitive electronic equipment since they will not generate or be affected by Electro Magnetic Interference (EMI). Moreover, since fiber is chemically passive and corrosion resistant, fiber optic sensors can be made biocompatible and suitable for biomedical applications. Low fiber transmission loss and high data bandwidth enable multiplexing of the signals from several sensors onto a single fiber channel while simplifying remote sensor interrogation.

Distributed fiber sensors are often referred to as D(X)S (where X represents the monitored parameter). In these systems, in addition to transmitting the data to an interrogator (i.e., a device that requests and receives data from the fiber sensors), the fiber also doubles as the sensor. Monitored variables can include Temperature (DTS), Acoustic oscillations (DAS), Strain (DSS), or Pressure (DPS). Because of the provided information content and ease of their deployment, distributed systems have been used in a variety of industries from Oil & Gas production (DTS and DAS) to perimeter security (DAS) and fire protection (DTS). However, unlike more mature systems, DTS and DAS, that have practically been commoditized, DSS and DPS have yet to move out of the laboratory.

Two different exemplary approaches for using optical fiber for distributed pressure measurement are presented: one technique is based on characterization of elastic (i.e., Rayleigh) scattering in Polarization Maintaining (PM) fibers; and the other relies on the monitoring of (inelastic) Brillouin scattering in regular (non-PM) Single Mode fibers (SMF) or Multi Mode fibers (MMF).

The Rayleigh-based DPS approach relies on measurement of the stress-induced birefringence inside PM fibers. Unlike SMF and MMF fibers that have cylindrically symmetrical cross section in order to minimize the Polarization Mode Dispersion (PMD), PM fibers usually feature symmetry breaking elements that introduce inherent birefringence required to separate the propagating polarization modes. Any change in pressure perturbs the stress distribution inside the fiber and affects its birefringence. Consequently, measurement of the local fiber birefringence can provide insight into the local pressure.

Figure 6:
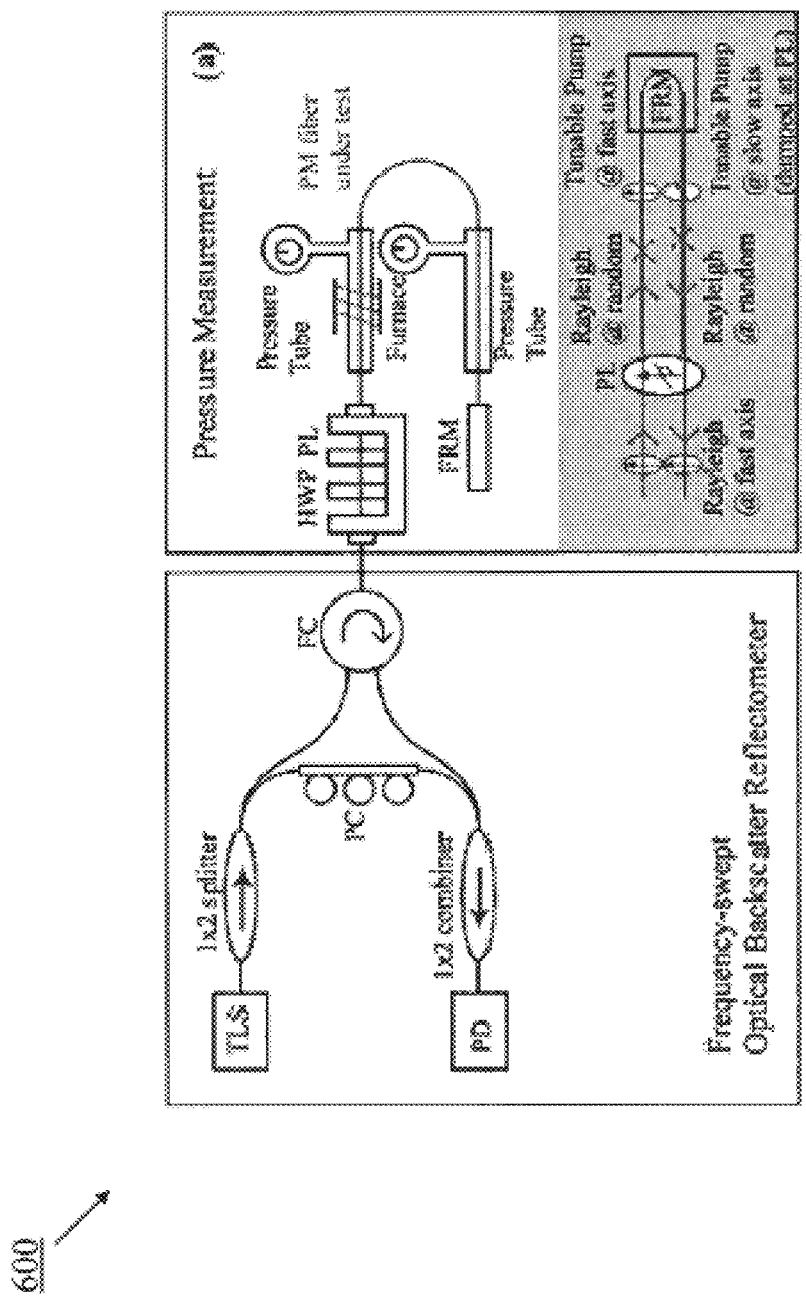
FIG. 6 is a diagram showing a Rayleigh-based distributed fiber sensor suitable for measuring soft tissue pressure, according to one exemplary embodiment.

A diagram 600 illustrating a typical setup for this method of operation is shown in FIG. 6. A frequency tunable output of a PM fiber coupled laser is split into two parts: One is used to illuminate the Fiber Under Test (FUT) while the other part is stored in a local interferometer arm to be used as a reference. When laser input undergoes Rayleigh backscattering in the FUT, the resultant photons are directed back to the receiver where they are interfered with a stored copy of light. Because Rayleigh scattering preserves the initial polarization state, the photodiode signal provides the information necessary to calculate the phase delay between the polarization modes. In turn, this information is used in order to estimate the PMD in the fiber and the ambient pressure.

The Brillouin-based DPS approach involves spectral characterization of the non-elastic Brillouin scattering in the fiber. The method takes advantage of the frequency dependence of the scattered line on fiber strain. In this case, the pressure acting on the fiber results in radial and axial forces on the fiber's glass structure. Via the photo-elastic effect these forces change the refractive index of the glass. This, in turn, affects the Brillouin backscattering spectrum. Consequently, by conducting spectrally resolved Optical Time Domain Reflectivity (OTDR) measurements, it becomes possible to measure the Brillouin line spectral shift and calculate local pressure in different fiber segments.

Figure 7:
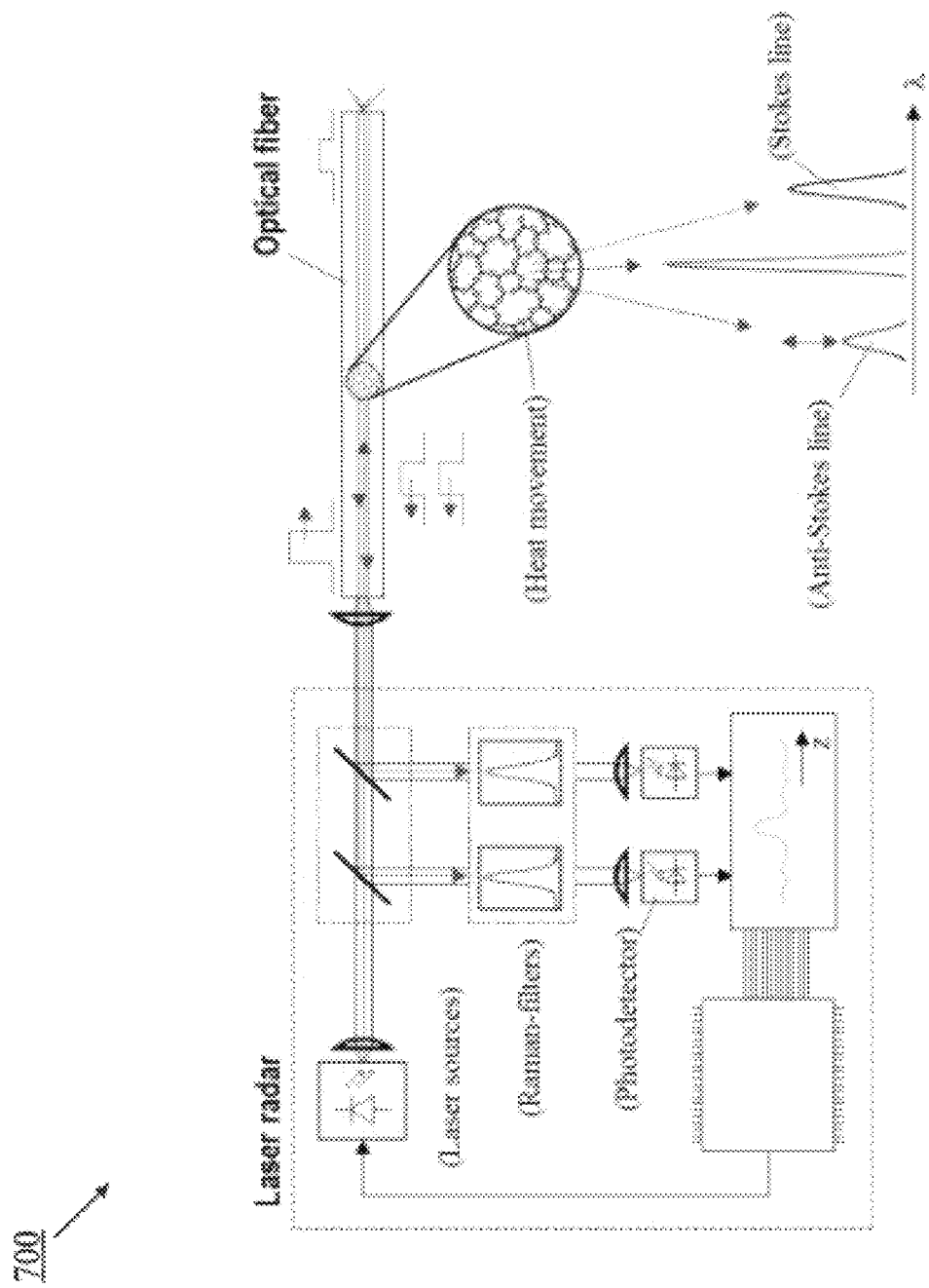
FIG. 7 is a diagram showing a Brillouin-based distributed fiber sensor suitable for measuring soft tissue pressure, according to one exemplary embodiment.

A diagram 700 illustrating a typical setup for this method of operation is shown in FIG. 7. The monitoring system consists of the Optical Module or Laser Source (DPS Controller) and the Fiber Optic cable embedded in an enclosure, for example, in a sleeve or medical tape. The laser light from the Controller is fed into the optical fiber and the actions of pressure at the sensor cable cause a molecular vibration within the glass fiber material that leads to light scattering (Rayleigh scattering) of the laser light. The light is reflected back to the DTS and the scattering (Raman Anti-Stokes line) is compared to a Reference value (Raman Stokes Line). This intensity value of light is proportional to the molecular vibration created by pressure, allowing for the pressure at linear locations of the glass fiber cable to be calculated. Spatial Resolution or location is determined by the amount of time it takes for the backscattered light to return to the detection unit in the (e.g., Brillouin-based) DPS.

While the Rayleigh method has been demonstrated to deliver sub-cm spatial resolution, it requires construction of a disposable sensor out of more expensive PM fiber as well as stabilization of the interrogating interferometer. The Brillouin method, on the other hand, enables very inexpensive sensor construction (cost of the regular SMF fiber can be just a few cents per foot); however, the detection stage requires spectral selectivity, potentially making it more expensive. The general inventive concepts contemplate that either of these approaches could be used.

As described herein, the general inventive concepts contemplate many configurations of optical sensors for monitoring soft tissue temperature and/or pressure.

In one exemplary embodiment, the optical sensors take the form of or otherwise are used in a custom or accurately fitted garment to be placed over a soft tissue of interest. The garment may be composed of stretchy (e.g., elastic) fabric or plastic. For example, the garment could take the form of a stocking to be placed underneath any immobilizing material (e.g., cast, splint) or directly on the skin surface alone.

In one exemplary embodiment, the custom-fitted, stretchy fabric or plastic encasing the fiber optic glass strands may contain antimicrobial or other interventional properties such as, but not limited to, antibiotic, silver, anti-inflammatory, or other medicine imprinting.

The exemplary embodiments disclosed herein find particular applicability in the health care arena by providing health care workers with useful, real-time information on traumatic edema, post-surgical swelling, iatragenic soft tissue injury, reperfusion injury, or immobilized extremity.

Various non-limiting, exemplary applications of the inventive technology are set forth below to further illustrate the general inventive concepts.

The optical sensors can be used to monitor pressure in paralyzed or immobile patients with high risk of tissue ischemia from excessive pressure points on all parts of body. For example, the optical sensors can be used to monitor pressure during pressure treatments for burn patients or peripheral edema.

Figure 8:
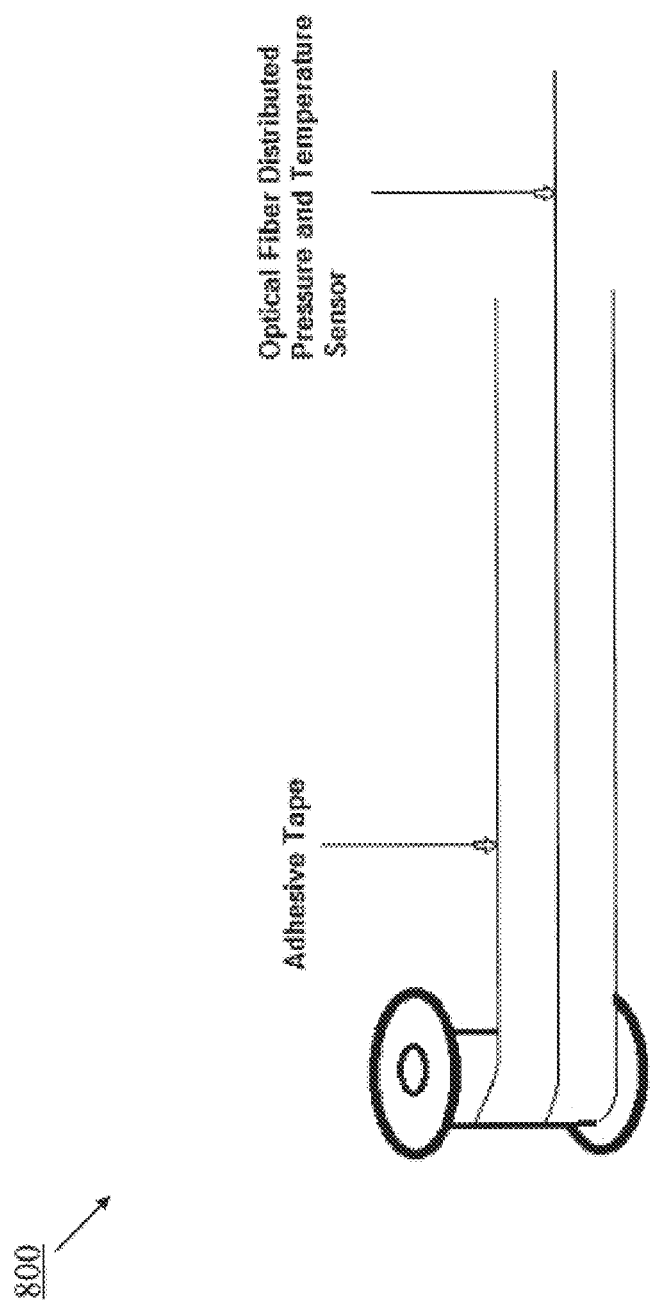
FIG. 8 is a diagram showing an example of adhesive tape embedded with an optical fiber pressure sensor.

FIG. 8 shows an exemplary adhesive tape 800 with an embedded optical fiber pressure sensor that could be applied to various portions of a patient's skin to monitor pressure in the underlying tissue.

The optical sensors can be placed in the lining of a splint or cast to provide pressure data in a post-surgical, post-traumatic, or other setting.

Figure 9:
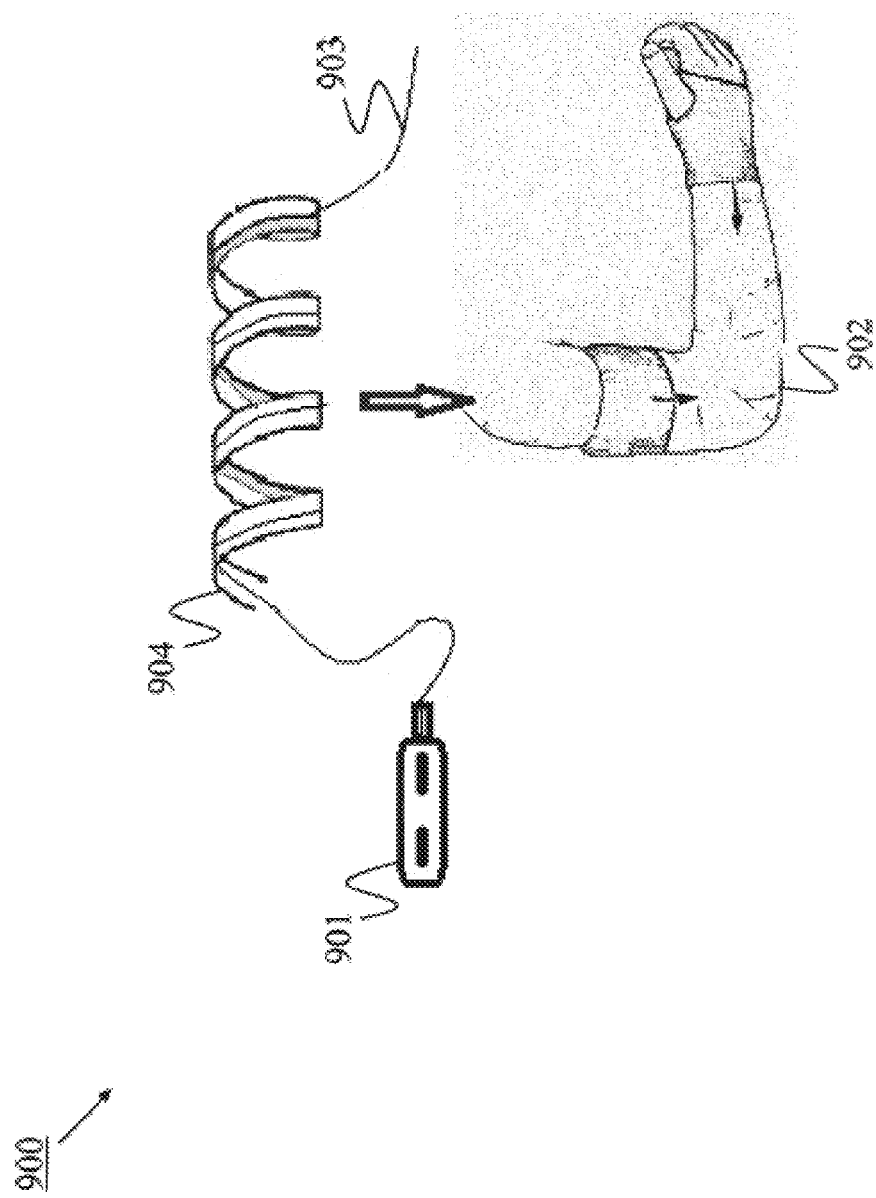
FIG. 9 is a diagram showing one exemplary embodiment of a system for monitoring pressure under an arm cast.

FIG. 9 shows an exemplary system 900 for monitoring such an application in the context of an arm cast. The system 900 includes an interrogator 901, the arm cast 902, a portion of an optical fiber pressure sensor cable 903 that extends outside the arm cast 902, and an adhesive tape 904 with a portion of the optical fiber pressure sensor cable embedded therein. The adhesive tape 904 is placed between the patient's arm and the arm cast 902.

Figure 10:
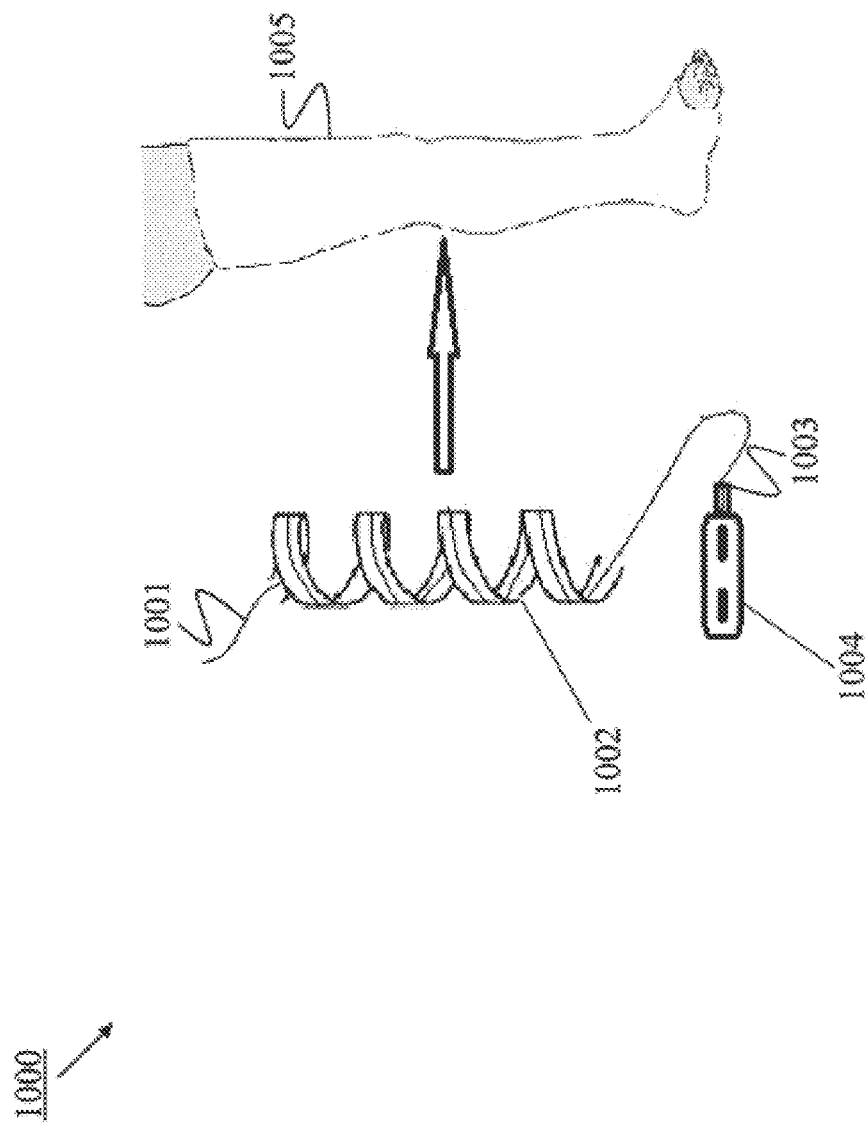
FIG. 10 is a diagram showing one exemplary embodiment of a system for monitoring pressure under a leg cast.

FIG. 10 shows an exemplary system 1000 for monitoring such an application in the context of a leg cast. The system 1000 includes an optical fiber pressure sensor cable 1001, an adhesive tape 1002 with a portion of the optical fiber pressure sensor cable embedded therein, and a connector/adaptor 1003 that interfaces the optical fiber pressure sensor cable to an interrogator or DPS controller 1004. The adhesive tape 1002 is applied to the patient's leg prior to a leg cast 1005 being applied.

Figure 11:
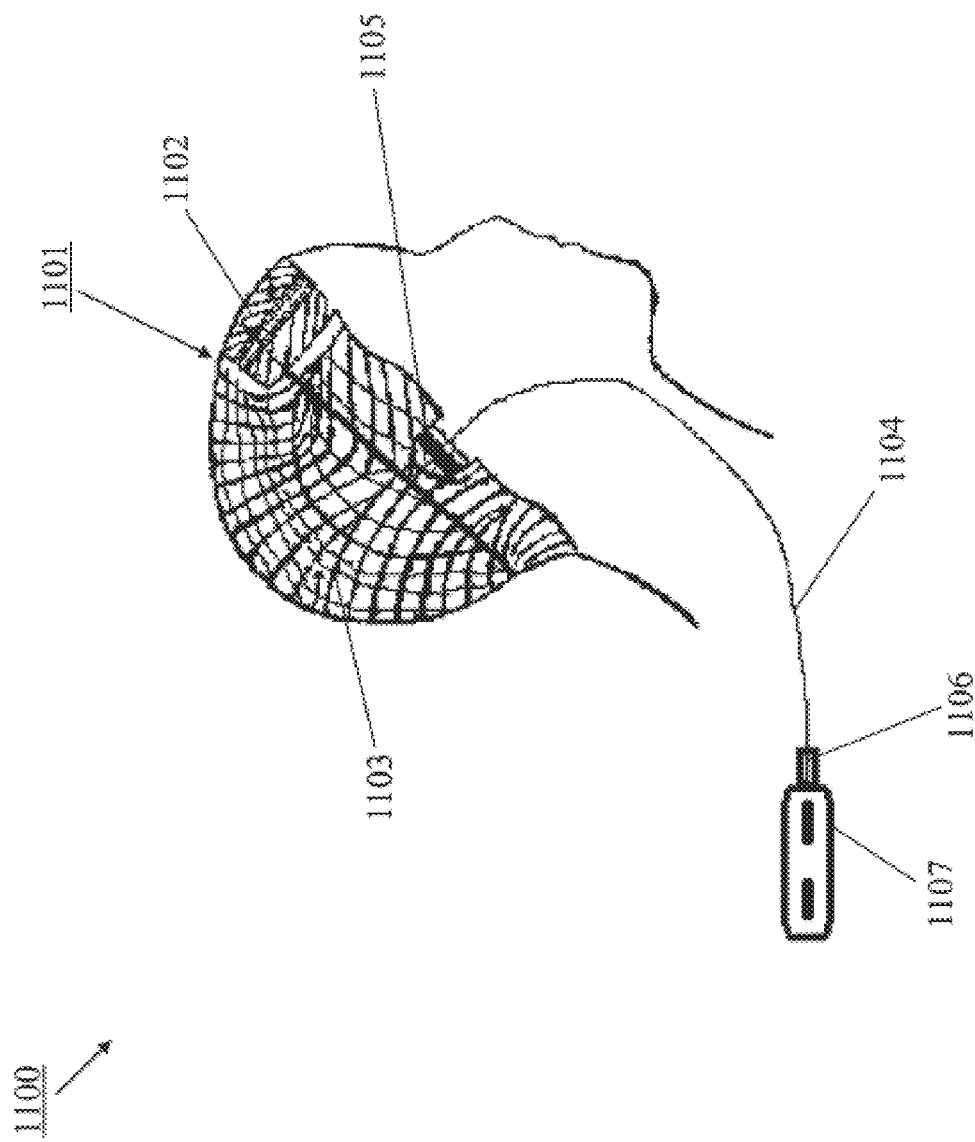
FIG. 11 is a diagram showing one exemplary embodiment of a system for monitoring pressure at or in proximity to the head of a patient.

FIG. 11 shows an exemplary system 1100 for monitoring such an application in the context of a head wrapping, bandage, cast, or similar structure. The system 1100 includes a mesh skull cap 1101 applied to the patient's head. The mesh skull cap 1101 includes a plurality of embedded optical fiber pressure sensor cables 1102, 1003. An optical fiber cable 1104 joins a connector 1105 of the skull cap 1101 to a connector 1106 of an interrogator or DPS controller 1107, thereby interfacing the skull cap 1101 and the interrogator 1107.

Figure 12:
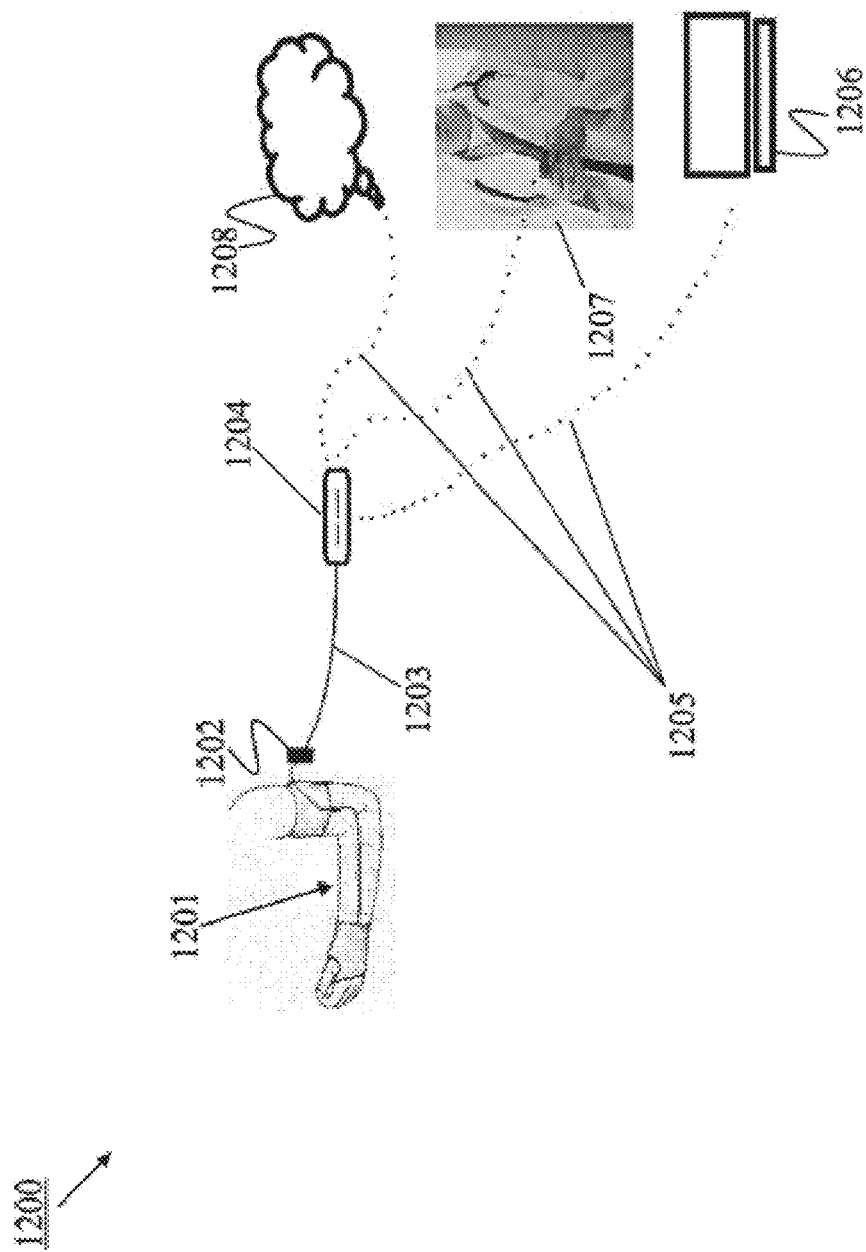
FIG. 12 is a diagram showing one exemplary embodiment of a system for monitoring pressure and temperature of tissue of a patient.

FIG. 12 shows a exemplary embodiment of a fiber optic pressure and temperature monitoring system 1200. The system 1200 includes a mesh sleeve or tape 1201 embedded with an optical fiber sensor cable. The sleeve 1201 is placed on the patient's skin to monitor the pressure and temperature of underlying tissue. The system 1200 also includes an optical fiber receptacle 1202 which facilitates connection of the optical fiber 1203 outside of the sleeve 1201 to a DPS controller 1204 (e.g., including an interrogator and a laser light source). The system 1200 uses one or more communication links 1205 (e.g., WiFi, BlueTooth, Ethernet) to send information to one or more devices for further processing. By way of example, the one or more devices could be a laptop 1206 or tablet (e.g., iPad) running corresponding interpretation software for further processing (e.g., performing any calculations on, displaying relevant output of) the information; a smart phone 1207 (e.g., iPhone) running a corresponding interpretation software smart phone application for further processing the information; or a secure server 1208 that receives the DPS information for remote interrogation and processing by appropriate medical staff.

Figure 13:
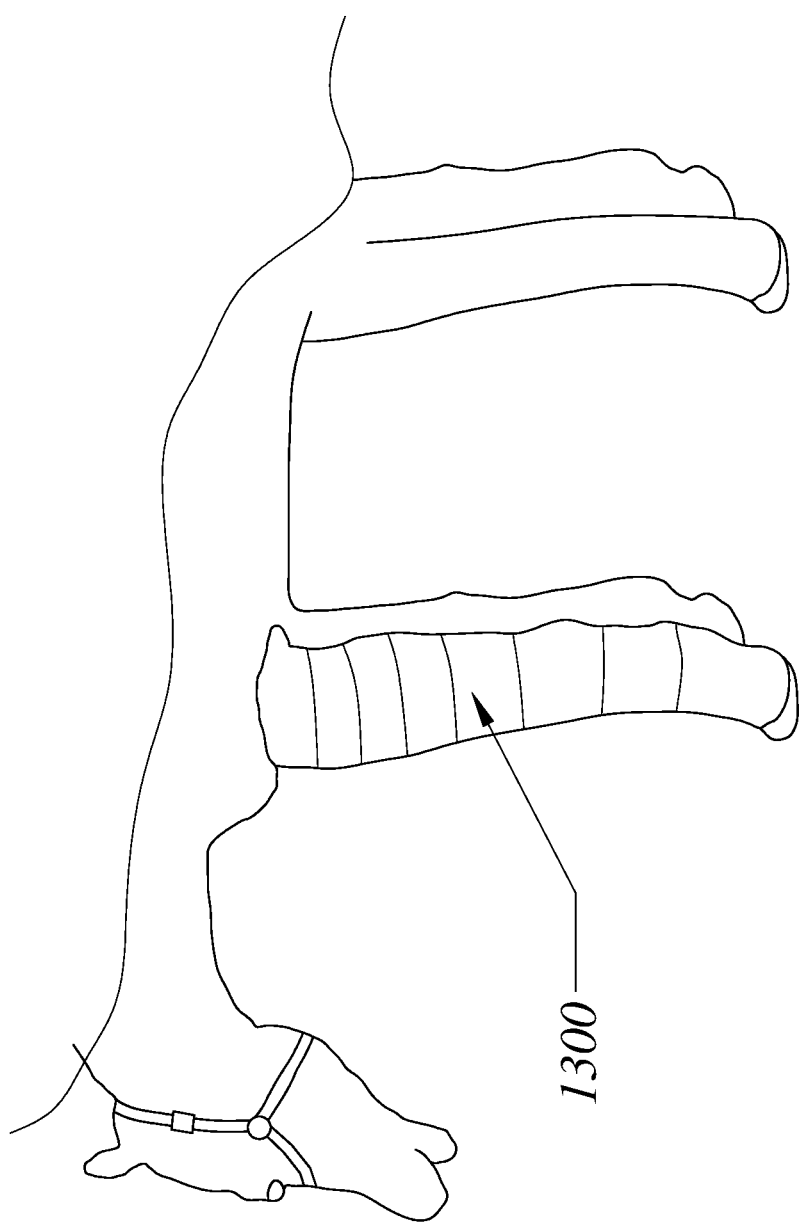
FIG. 13 is an image representing one exemplary embodiment of monitoring pressure/temperature of tissue in a horse.

FIG. 13 represents an exemplary application of the pressure/temperature monitoring systems described herein in the context of a leg cast 1300 of a non-human patient, i.e., a horse.

Figure 14:
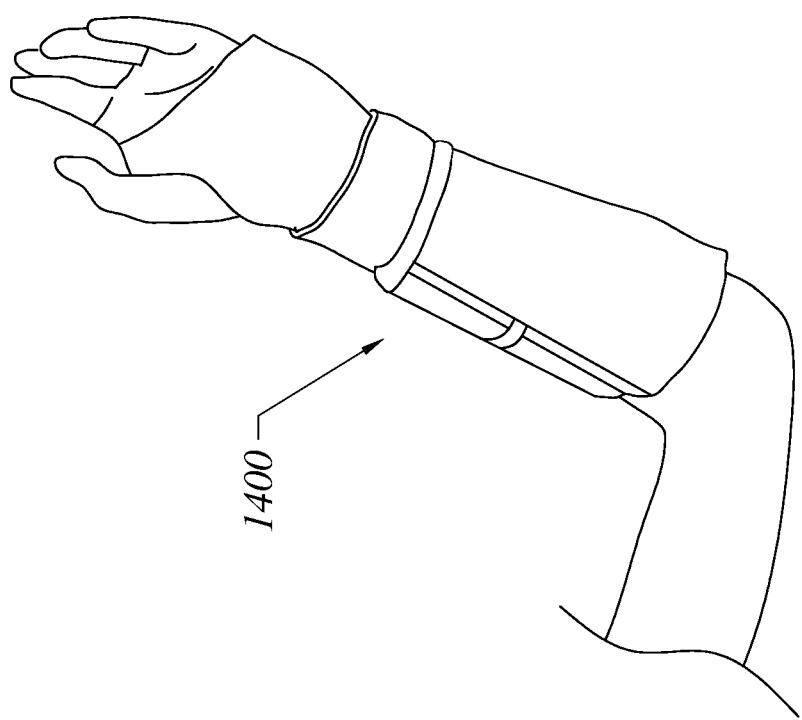
FIG. 14 is an image representing one exemplary embodiment of monitoring pressure/temperature by use of an optical fiber sensor in conjunction with a removable arm brace.

FIG. 14 represents an exemplary application of the pressure/temperature monitoring systems described herein in the context of a removable arm brace or splint 1400.

Figure 15:
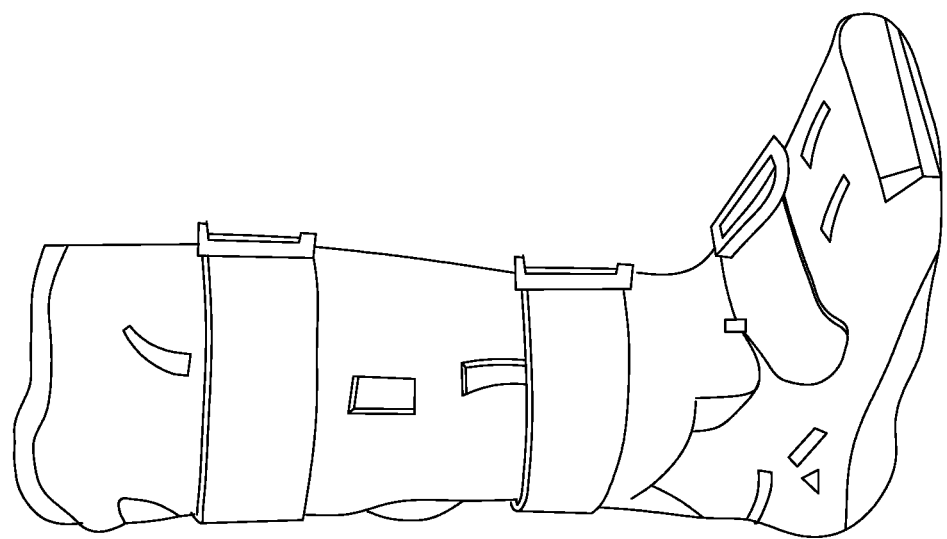
FIG. 15 is an image representing one exemplary embodiment of monitoring pressure/temperature by use of an optical fiber sensor in conjunction with a removable foot brace.

FIG. 15 represents an exemplary application of the pressure/temperature monitoring systems described herein in the context of a removable foot boot or splint 1500.

Figure 16:
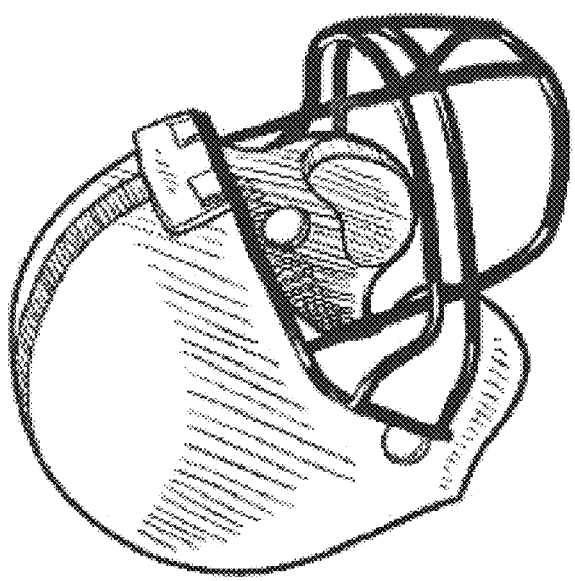
FIG. 16 represents one exemplary embodiment of monitoring pressure/temperature by use of an optical fiber sensor in conjunction with a football helmet.

As another example, the optical sensors can be used to collect or monitor information in athletic environments, such as through helmet lining for impact forces, overuse injury in running sports, etc. In this regard, FIG. 16 represents an exemplary application of a pressure/temperature monitoring system described herein in the context of a football helmet 1600.

Figure 17:
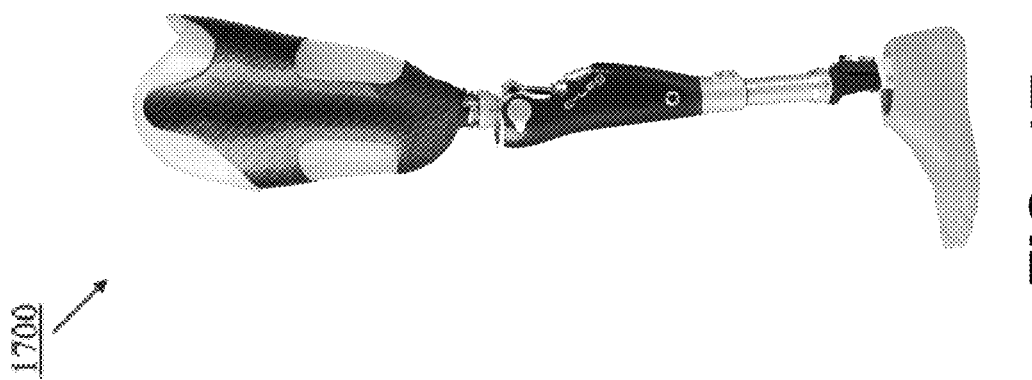
FIG. 17 represents one exemplary embodiment of monitoring pressure/temperature by use of an optical fiber sensor in conjunction with a prosthetic leg.

FIG. 17 shows an exemplary application of the pressure/temperature monitoring systems described herein in the context of a prosthetic limb 1700 (e.g., a prosthetic leg). In this manner, the monitoring systems could measure pressure and/or temperature of tissue in proximity of the region of the residual limb where the prosthetic limb is coupled to the patient. For example, the monitoring systems could measure or otherwise detect any swelling at the interface between the prosthetic device and the residual limb.

In the surgical amphitheater, mitigating excessive pressures on a patient's body can prove challenging. In fact, surgery-related pressure ulcers are the most common hospital-acquired ulcers. When a patient undergoes general anesthesia, blood pressure drops and thus tissue perfusion is lowered. This assists with intraoperative blood loss, but can lead to shunting towards more vital structures other than the skin (i.e. organs). While the patient is immobile, long periods of increased pressure on the skin at any location can lead to blistering, breakdown and even tissue death while in the operating room or in the perioperative period.

Paralytics and neuromuscular depolarizing agents are medications commonly employed in the operating room. The benefits of administration are improved ventilation and limitation of involuntary patient movement during surgery. A consequence of paralytic use, however, is loss of muscle tone. The paralyzed muscle can no longer contract and blood pooling occurs over dependent areas. Bony areas devoid of muscle or adequate soft tissue coverage are prone to increased and dangerous pressure levels within the overlying skin when surrounding muscle no longer shields focalization. With sedation, the patient often cannot feel the effects of prolonged pressure even in the postoperative period. Sustained pressures at or greater than 30 mmHg exceed capillary perfusion pressure and leads to cellular death and skin ulceration.

Risk factors associated with surgery-related pressure ulcers have been identified. Ulcers can occur with pressure, shear force, and friction. High risk criteria include long operating times (>3 hours), body mass index (BMI)<19 or >40, patients with baseline impaired sensation, and neurosurgical, cardiac, vascular, trauma, transplant and bariatric procedures.

To combat excessive pressures over bony prominences, the use of various padding materials has been implemented. Multi-density foam cores, porous foams, gel, laminated vinyl fabric, pillows, and thick cottons are a few examples of the types of padding materials that are currently used. These padding materials are placed in areas with minimal soft tissue protection over bony prominences such as elbows, knees, heels, hips and head. However despite a strong awareness of the problem, the incidence of surgical-related pressure ulcers has been reported in as high as 8.5% of all cases. See Chen H L, Chen X Y, Wu J., *The Incidence of Pressure Ulcers in Surgical Patients of the Last 5 Years: A Systematic Review*, Wounds, 2012 Sep. 24 (9):234-41, PMID: 25874704.

The use of fiber optic sensors embedded in a flexible tape according to the general inventive concepts may be employed to mitigate the aforementioned negative effects of excessive pressures on a patient's body during surgery. In this regard, exemplary embodiments of an optic sensor embedded flexible tape may be aimed at alerting health care personnel to elevated and sustained pressures along the strip in its entire length. In some embodiments, the strip itself may also be padded with gels, silicone, and fabrics so that the strip itself additionally assists in pressure offloading. A goal of using such a fiber optic strip is to receive feedback that can be used to provide the most even pressure distribution possible over prone areas of skin breakdown initially, and also awareness of areas of the skin that become subjected to elevated pressures over time.

Operating room headrests are notorious for causing occiput and facial pressure sores when the patient is placed in a prone or supine position. The weight of the head and gravity can easily exceed capillary perfusion pressures and as such, great care is used to pad these areas intraoperatively. However, sometimes too much padding can itself cause excessive pressure in particular areas if placed unevenly. If the face is too large, excessive pressures can be placed on the eyes when they are placed over the headrest. If the face is too small, it will fall through the middle as in pediatric patients and cause focal pressure on the cheeks. Such a problem can be visualized with respect to the horseshoe shaped headrests of FIGS. 18A-19B, to which the general inventive concepts described in the disclosure have been applied.

FIGS. 18A and 18B represent one exemplary embodiment of a soft tissue monitoring system 1800 for use in an operating room, particularly in conjunction with the headrest 1805 of an operating table 1810. As can be observed in FIG. 18B, in this particular example, the headrest is located and oriented so as to support the head of a patient 1815 from the rear while the patient is in a supine position.

As shown FIGS. 18A and 18B, a fiber optic strip 1820 has been placed along the headrest 1805 in an area that will underlie and support the patient's head during surgery. The fiber optic strip 1820 may be of a construction described above such that the fiber optic strip has the ability to sense pressure applied thereto by the tissue of the patient's head. The fiber optic strip 1820 may be connected to an interrogator and/or to other operating room monitoring equipment so as to provide an indication of the pressure being exerted on the patient's head by the headrest 1805. This would help the medical personnel in the operating room understand where there might be deficiencies in padding and the location of excessive pressures.

FIGS. 19A and 19B represent an alternative exemplary embodiment of a soft tissue monitoring system 1900 for use in an operating room, particularly in conjunction with the headrest 1905 of an operating table 1910. As can be observed in FIG. 19B, in this particular example, the headrest is located and oriented so as to support the head of a patient 1915 from the front, such as in the cheek and forehead areas as indicated, while the patient is in a prone position.

As shown FIGS. 19A and 19B, a fiber optic strip 1920 has been placed along the headrest 1905 in an area that will underlie the patient's face and support the patient's head during surgery. The fiber optic strip 1920 may again be of a construction described above such that the fiber optic strip has the ability to sense pressure applied thereto by the tissue of the patient's face. The fiber optic strip 1920 may again be connected to an interrogator and/or to other operating room monitoring equipment so as to provide an indication of the pressure being exerted on the patient's face by the headrest 1905. Use of the fiber optic strip 1920 can provide medical personnel in the operating room with real-time information on the pressure near the areas of interest, and would help the medical personnel understand where there might be deficiencies in padding and the location of excessive pressures.

Out of necessity, surgical tables are often minimally padded, ruggedly built for longevity with simplicity in design for function and ease of sterilization. Certain patient body areas, such as for example, the elbows, gluteal areas, heels, ankles, knees, and hips must be closely monitored for areas of inadequately padding. The surgical team and anesthesiology team both check to ensure proper prophylactic cushioning.

To this end, FIGS. 20A and 20B represent exemplary embodiments of a soft tissue monitoring system 2000 for use in an operating room, particularly in conjunction with an operating table 2005, for monitoring various pressure points on the patient's body 2010 while the patient lies in a supine (FIG. 20A) or prone position (FIG. 20B). As part of the system 2000 according to the general inventive concepts of the disclosure, fiber optic strips, patches, etc., 2015 may be placed along one, some or all such body areas that might witness higher pressures over the course of an operation due to contact with the operating table. A fiber optic strip 2015 may also be placed under the patient's head for the same purpose.

The fiber optic strips 2015 may again be of a construction described above such that the fiber optic strips have the ability to sense pressure applied thereto by the indicated points of contact between the patient and the operating table 2005. The fiber optic strips 2015 may again be connected to an interrogator (not shown) and/or to other operating room monitoring equipment so as to provide an indication of the pressure being exerted at said contact points by the operating table 2005. Use of the fiber optic strips 2015 can provide medical personnel in the operating room with real-time information on the pressures at or near the areas of interest.

FIGS. 21A and 21B represent another soft tissue monitoring system 2100 for use in an operating room, particularly in conjunction with a surgical beanbag 2105, such as those used when a patient is placed in a lateral position (FIG. 21B), and along calves/heels when legs are placed in stirrups during lithotomy position for obstetrical/gynecological or colorectal procedures. The system 2100 may again be used for monitoring various pressure points on the patient's body 2110 while the patient lies on the beanbag 2105.

As part of the system 2100 according to the general inventive concepts of the disclosure, fiber optic strips or tape 2115 may be used to line the beanbag 2105. The fiber optic strips 2115 may again be of a construction described above such that the fiber optic strips have the ability to sense pressure applied to the tissue of the patient by the beanbag 2115. The fiber optic strips 2115 may again be connected to an interrogator 2120 and/or to other operating room monitoring equipment so as to provide an indication of the pressure being exerted on the patient by the beanbag 2105. Use of the fiber optic strips 2115 can provide medical personnel in the operating room with real-time information on the pressures at or near areas of interest on the patient. The same monitoring equipment and interrogator 2120 can be utilized at the end of the case for intraoperative placement of casts and splints when the patient is asleep and not able to notify the cast or splint applicator of a too tight or too loose placement.

Figure 22:
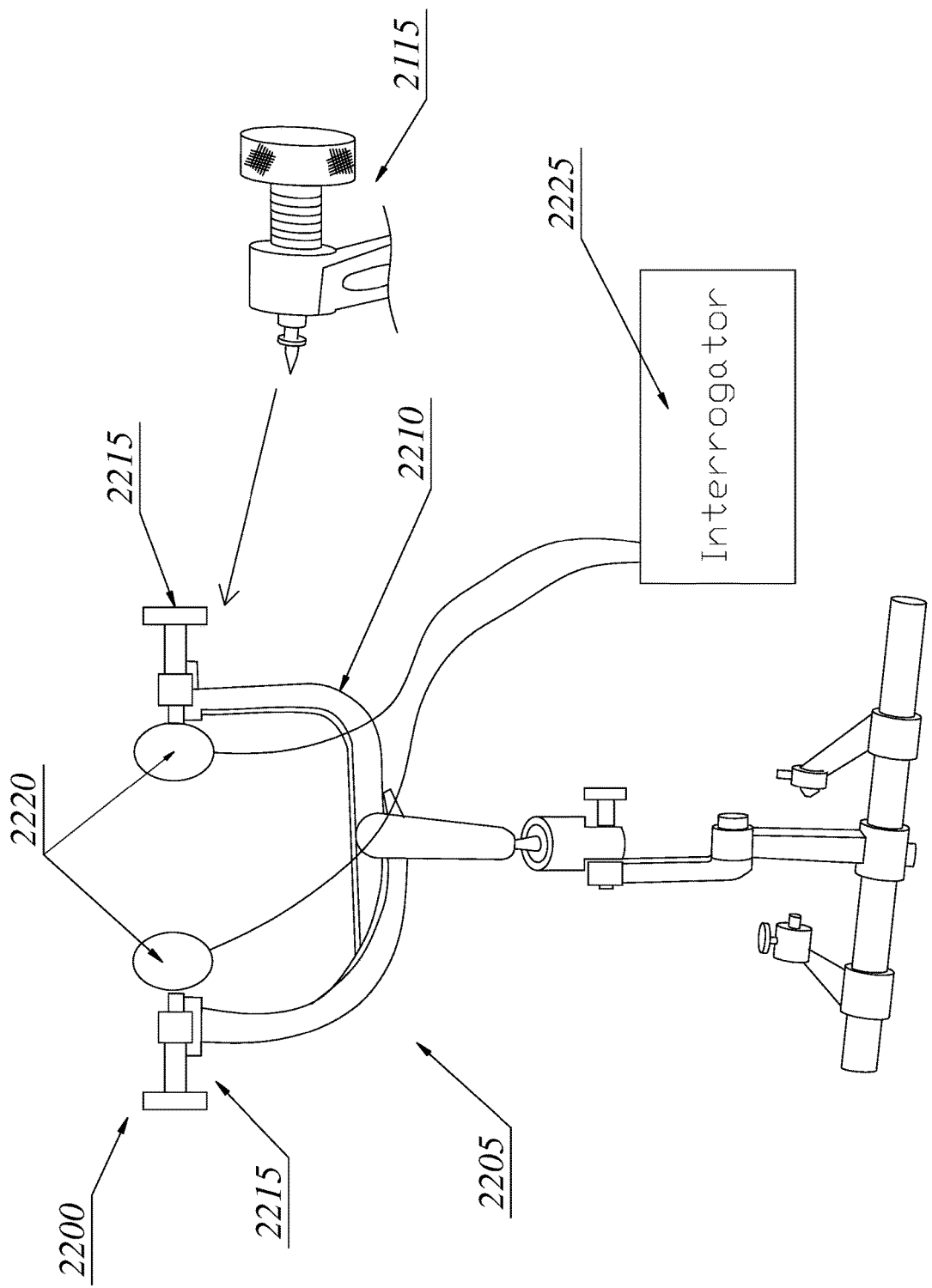
FIG. 22 illustrates another exemplary embodiment of a soft tissue monitoring system for use in an operating room, particularly in conjunction with a skull clamp/headrest device.

FIG. 22 represents another exemplary embodiment of a soft tissue monitoring system 2200 for use in an operating room, particularly in conjunction with a skull clamp/headrest device 2205, such as a Mayfield® three-pin skull clamp. Such clamps are designed generally to securely affix the head of a patient to the operating table during certain neurosurgery procedures. The patient's head is placed and aligned within a horseshoe-shaped frame 2210 of the skull clamp, which is attached to an operating table, and the position of the patient's head is secured by tightening a plurality of pins 2215 (usually three) against the patient's head to a predetermined pressure.

As shown, fiber optic strips or tape 2220 may be placed on the head of the patient at the location of each pin 2215. The fiber optic strips 2220 may again be of a construction described above such that the fiber optic strips have the ability to sense pressure applied to the head of the patient by the pins 2115 of the skull clamp. The fiber optic strips 2220 may again be connected to an interrogator 2225 and/or to other operating room monitoring equipment so as to provide an indication of the pressure being exerted on the head of the patient by the pins 2215. Use of the fiber optic strips 2220 can provide medical personnel in the operating room with real-time information on the pressures at the points of pin contact with the patient's head, thus avoiding inadvertent penetration of certain delicate skull bones, etc.

Figure 23B:
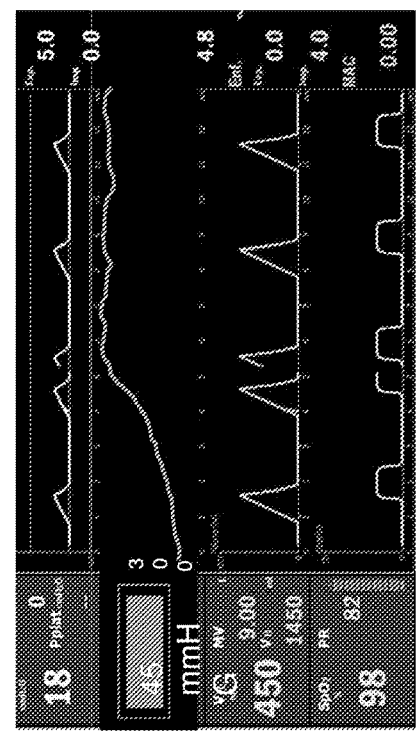
FIGS. 23A and 23B illustrate another exemplary embodiment of using an optical fiber based monitoring system in an operating room, particularly in conjunction with anesthesia monitoring of pressure with ventilation.
Figure 23A:
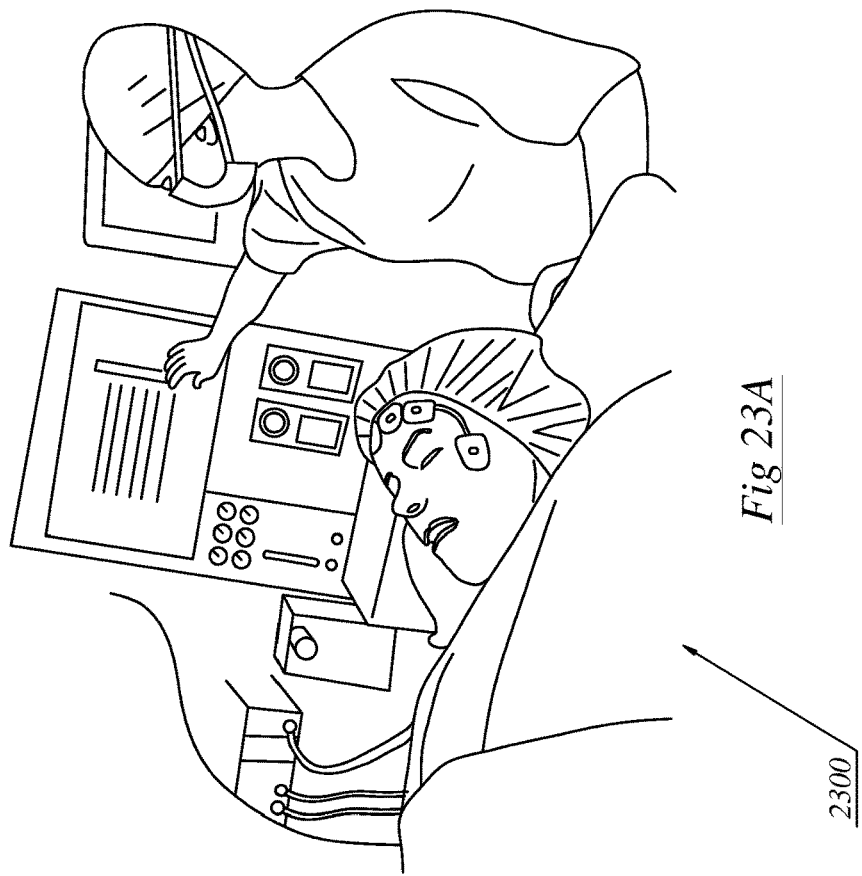

In other alternative embodiments, fiber optic strips can be placed in areas that are not normally subjected to pressure during an operation. For example, fiber optic strips may be placed at the ventral abdomen in neurosurgical patients where increasing venous return in the abdomen can effect intracranial bleeding. As represented by the exemplary anesthesia monitoring of pressure with ventilation system 2300 of FIGS. 23A and 23B, such atypical pressures could again be monitored in real time and added to the multifunction patient monitor 2305 that is available to both surgeon and anesthesiologist for notification and monitoring.

Advantages to using fiber optic technology in the operating room are numerous. Monopolar electrocautery, the most common tissue-cutting, hemostatic instrument, requires the patient to be grounded and not have any metal touching the patient for risk of burns and/or fires. Other forms of pressure monitoring such as piezoelectric fabric or strain gauges use either metal or electricity to assist in measuring pressure. The glass is inert and the light passed through it are unaffected by MRI, or other current intraoperative imaging modalities. It would also not cause confusion like many precordial EKG leads which contain metal when the patient is x-rayed. The disposable nature of the fiber optic strip makes clean up simple and usable on the floors after the patient leaves the operating room.

Figure 24:
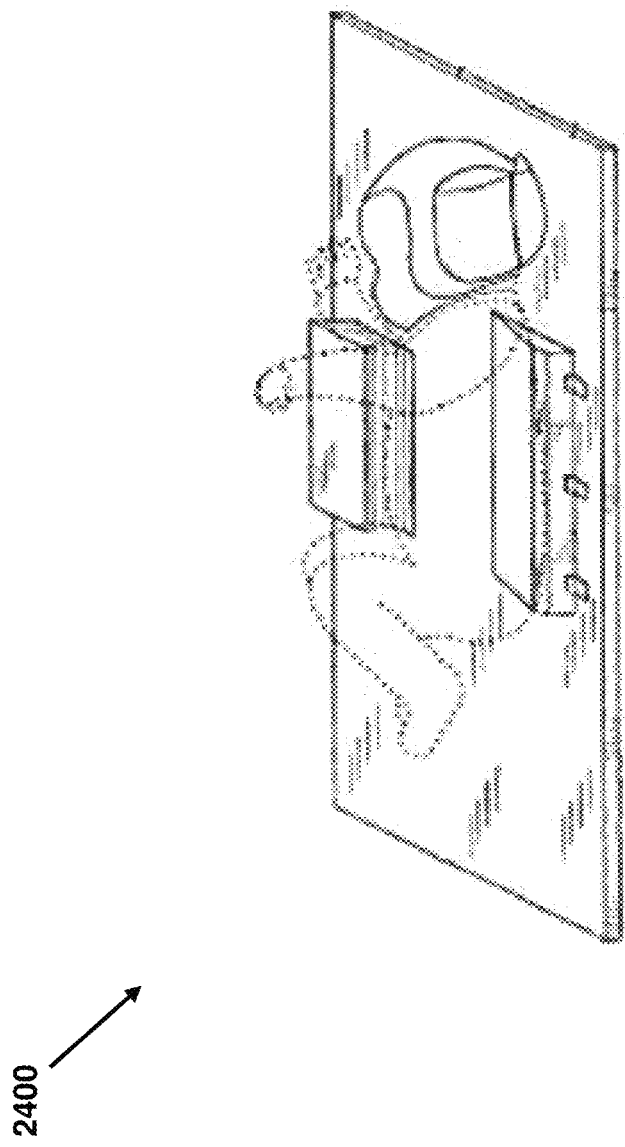
FIG. 24 illustrates one exemplary embodiment of a soft tissue monitoring system using an optical fiber sensor in conjunction with a sleeping pad.

The general inventive concepts may also have applications beyond monitoring a patient's tissue. For example, FIG. 24 shows an exemplary application of the fiber optic sensor technology in the context of a pad 2400 on which an infant or young child would rest or sleep. The pad 2400 uses one or more fiber optic sensors to measure or otherwise detect movement of the child. The fiber optic sensors can also be used to measure the body temperature of the child.

The general inventive concepts may also have applications beyond monitoring a patient. For example, the general inventive concepts may have utility in the realm of sports, such as for the purpose of determining the level of "readiness" or sufficient perfusion to an extremity or underlying muscle. Such a determination may be accomplished, for example, by employing a fiber optic strip or tape embodiment of the disclosure to measure the skin temperature of an athlete at a soft tissue area of concern. Basically, captured heat data could be used to help determine if the muscle(s) in the monitored area are sufficiently warm, so as to prevent injury from inadequate pre-use warm up.

From the above description of exemplary embodiments, those skilled in the art will not only understand the general inventive concepts and attendant improvements, but will also find apparent various changes and modifications to the structures and methods disclosed. For example, although the monitoring of soft tissue, as described herein, focuses on the pressure and temperature of the tissue, it might be possible to monitor other features of the tissue using the inventive optical sensing platform presented herein. Furthermore, localized measures of pressure, temperature, and the like need not be limited to tissue. It is sought, therefore, to cover all such changes and modifications as fall within the spirit and scope of the general inventive concepts, as defined by any appended claims, and equivalents thereof. Therefore, while certain exemplary embodiments are described in detail above, the scope of the general inventive concept is not considered limited by such disclosure, and modifications are possible without departing from the spirit of the invention as evidenced by the following claims:

What is claimed is:

1. A soft tissue pressure monitoring system, comprising:
   a source of optically pumped light for one or more optical fibers, wherein the source of optically pumped light is either a laser, a light emitting diode or an ultraviolet generator;
   an optical sensor provided as a moisture resistant adhesive tape strip adapted for application about the soft tissue; the moisture resistant adhesive tape strip having at least one of the optical fibers distributed therein and running the length of the moisture resistant adhesive tape strip, wherein changes in the volume of the soft tissue contacting the moisture resistant adhesive tape strip alter a refraction of light carried by the at least one of the optical fibers connected to the source of optically pumped light;
   a controller including an interrogator; the controller connected to the source of optically pumped light and at least one of the optical fibers;
   an interface connecting a data processing device to the controller;
   wherein the optically pumped source of light is configured to input optically pumped light into the at least one of the optical fibers and the controller is configured to receive light returned from the at least one of optical fibers; the data processing device programmed to repeatedly measure the amount of light returned by the at least one of the optical fibers to the controller such that the data processing device utilizes changes in the refractions of light carried by the at least one of the optical fibers to calculate internal pressures of the soft tissue and to trigger an audible and/or visible alarm when calculated internal pressures of the soft tissue exceed a preselected threshold; and wherein the at least one of the optical fibers is:
   a) a flexible distributed pressure measuring optical fiber, in contact with the soft tissue, including internal symmetry breaking elements introducing stress-induced birefringence adapted to assist in creating detectable Rayleigh backscattering; the optically pumped source of light split prior to entry into the flexible distributed pressure measuring optical fiber such that a first portion of optically pumped light is received by the flexible distributed pressure measuring optical fiber and a second portion of the optically pumped light is received by a local interferometer arm, wherein the optically pumped light stored in the local interferometer arm and the Rayleigh backscattering are compared by the data processing device in calculating the internal pressures of the soft tissue; or
   b) a flexible distributed pressure measuring optical fiber, receiving optically pumped light passed through a Raman filter, in contact with the soft tissue; the soft tissue creating radial and axial forces, along the length of the flexible distributed pressure measuring optical fiber, wherein contact of the soft tissue alters the radial and axial forces applied to the flexible distributed pressure measuring optical fiber and the refractive index of the flexible distributed pressure measuring optical fiber creating detectable Brillouin backscattering, Raman Stokes lines and Raman Anti-Stokes lines compared by the data processing device in calculating the internal pressures of the soft tissue.

2. The system of claim 1, wherein the flexible distributed pressure measuring optical fibers are distributed in a pattern selected from the group consisting of a matrix, a spiral, a honeycomb, and a double layer.

3. The system of claim 1, wherein the controller is a DPS controller adapted to determine pressure at specific locations along the length of the optical sensor, and wherein the DPS controller also includes the source of optically pumped light.

4. The system of claim 1, wherein the data processing device is selected from the group consisting of a personal computer, a laptop computer, a tablet, a smart phone, and a medical monitor.

5. The system of claim 1, wherein the data processing device further includes a display for outputting information collected by the controller in a form selected from the group consisting of a written report, a chart, a graph, a 3-D map indicating pressure readings with spatial recognition along the at least one optical fiber, and combinations thereof.

6. The system of claim 1, wherein the interface is a wired or wireless network or other communication connection.

7. The system of claim 1, wherein the interface is integrated with the data processing device.

8. The system of claim 1, further comprising software associated with the data processing device for processing time, wavelength and intensity information collected by the controller from the optical sensor.

9. The system of claim 1, wherein the optical sensor is adapted for placement at a location(s) on a patient that will support the patient through contact with an operating room patient support device, and wherein the optical sensor is connected to a data processing device configured as an operating room monitor.

10. The system of claim 1, wherein the adhesive tape strip is adapted for spiral wrapping of the adhesive tape strip around a body part of a patient.

11. The system of claim 1, further comprising a padding layer distributed along at least a tissue-contacting side of the adhesive tape strip.

12. The system of claim 11, wherein the padding layer is comprised of silicone.

13. The system of claim 1, further comprising an antimicrobial agent in the form of an antibiotic, silver, or an anti-inflammatory applied to the adhesive tape strip material.

14. A soft tissue pressure monitoring system, comprising:
   a source of optically pumped light for one or more optical fibers, wherein the source of optically pumped light is either a laser, a light emitting diode or an ultraviolet generator;
   an optical sensor provided as a moisture resistant adhesive tape strip adapted for application about the soft tissue; the moisture resistant adhesive tape strip having at least one optical fiber distributed therein and running the length of the moisture of the moisture resistant adhesive tape strip, wherein changes in the volume of the soft tissue contacting the moisture resistant adhesive tape strip alter a refractions of light carried by the at least one optical fiber connected to the source of optically pumped light;
   an antimicrobial agent in the form of an antibiotic, silver, or an an anti-inflammatory applied to the moisture resistant adhesive tape strip;
   a controller including an interrogator; the controller connected to the source of optically pumped light and the at least one optical fiber;
   an interface connecting a data processing device to the controller;
   wherein the source of optically pumped light is configured to input light into the at least one optical fiber and the controller is configured to receive light returned from the at least one optical fiber; the data processing device is programmed to repeatedly measure the amount of light returned by the at least one optical fiber to the controller such that the data processing device utilizes changes in refractions of light carried by the at least one optical fiber to calculate internal pressures of the soft tissue and to trigger an audible and/or visible alarm when calculated internal pressures of the soft tissue exceed a preselected threshold; and wherein the at least one of the optical fibers is:
   a) a flexible distributed pressure measuring optical fiber, in contact with the soft tissue, including internal symmetry breaking elements introducing stress-induced birefringence adapted to assist in creating detectable Rayleigh backscattering; the optically pumped source of light split prior to entry into the flexible distributed pressure measuring optical fiber such that a first portion of optically pumped light is received by the flexible distributed pressure measuring optical fiber and a second portion of the optically pumped light is received by a local interferometer arm; wherein the optically pumped light stored in the local interferometer arm and the Rayleigh backscattering are compared by the data processing device in calculating the internal pressures of the soft tissue; or
   b) a flexible distributed pressure measuring optical fiber, receiving optically pumped light passed through a Raman filter, in contact with the soft tissue; the soft tissue creating radial and axial forces, along the length of the flexible distributed pressure measuring optical fiber, wherein contact of the soft tissue alters the radial and axial forces applied to the flexible distributed pressure measuring optical fiber and the refractive index of the flexible distributed pressure measuring optical fiber creating detectable Brillouin backscattering, Raman Stokes lines and Raman Anti-Stokes lines compared by the data processing device in calculating the internal pressures of the soft tissue.

15. The system of claim 14, further comprising a padding layer distributed along at least a tissue-contacting side of the adhesive tape strip.

16. A soft tissue pressure monitoring system, comprising:
   a source of optically pumped light connected to one or more optical fibers wherein the source of light inputs optically pumped light into the one or more of the optical fibers and a controller receives light returned from the one or more optical fibers;
   a moisture resistant adhesive tape strip, adapted for application to the soft tissue, comprising the one or more optical fibers, wherein changes in the volume of the soft tissue contacting the moisture resistant adhesive tape strip alter a refraction of light carried by the one or more optical fibers;
   a controller including an interrogator; the controller connected to the source of optically pumped light and the one or more optical fibers; and
   a data processing device interfaced with the controller, wherein the data processing device is programmed to repeatedly measure the amount of light returned by the one or more optical fibers to the controller such that the data processing device utilizes changes in the refractions of light carried by the one or more optical fibers to calculate internal pressures of the soft tissue and to trigger an audible and/or visible alarm when calculated internal pressures of the soft tissue exceed a preselected threshold; and wherein at least one of the optical fibers is:
   a) a flexible distributed pressure measuring optical fiber, in contact with the soft tissue, including internal symmetry breaking elements introducing stress-induced birefringence adapted to assist in creating detectable Rayleigh backscattering; the optically pumped source of light split prior to entry into the flexible distributed pressure measuring optical fiber such that a first portion of optically pumped light is received by the flexible distributed pressure measuring optical fiber and a second portion of the optically pumped light is received by a local interferometer arm, wherein the optically pumped light stored in the local interferometer arm and the Rayleigh backscattering are compared by the data processing device in calculating the internal pressures of the soft tissue; or
   b) a flexible distributed pressure measuring optical fiber, receiving optically pumped light passed through a Raman filter, in contact with the soft tissue; the soft tissue creating radial and axial forces, along the length of the flexible distributed pressure measuring optical fiber, wherein contact of the soft tissue alters the radial and axial forces applied to the flexible distributed pressure measuring optical fiber and the refractive index of the flexible distributed pressure measuring optical fiber creating detectable Brillouin backscattering, Raman Stokes lines and Raman Anti-Stokes lines compared by the data processing device in calculating the internal pressures of the soft tissue.

17. The system of claim 16, wherein the data processing device further includes a display for outputting information collected by the controller in a form selected from the group consisting of a written report, a chart, a graph, a 3-D map indicating pressure readings with spatial recognition along the one or more optical fibers.

18. The system of claim 17, further comprising a padding layer distributed along at least a tissue-contacting side of the moisture resistant adhesive tape strip.

19. The system of claim 16, wherein an interface with the controller is a wired or wireless network or other communication connection.

20. The system of claim 16, further comprising software associated with the data processing device for processing time, wavelength and intensity information collected by the controller from the optical sensor.

\* \* \* \* \*